United States Patent [19]

Vigh et al.

[11] Patent Number: 5,614,072
[45] Date of Patent: Mar. 25, 1997

[54] INCREASED EFFICIENCY OF ELECTROPHORETIC SEPARATIONS BY MOBILITY MATCHING

[75] Inventors: Gyula Vigh, Magnolia, Tex.; Yasir Y. Rawjee, Conshohocken, Pa.; Robert L. Williams, Jr., Brian, Tex.

[73] Assignee: The Texas A&M University, College Station, Tex.

[21] Appl. No.: 359,641

[22] Filed: Dec. 20, 1994

[51] Int. Cl.$^6$ .................................................. G01N 27/26
[52] U.S. Cl. .......................... 204/450; 204/468; 204/549; 204/645
[58] Field of Search ........................... 204/180.1, 182.8, 204/183.3, 450, 468, 549, 645

[56] References Cited

U.S. PATENT DOCUMENTS 5,192,405  3/1993  Peterson et al. ...................... 204/180.1

OTHER PUBLICATIONS

M. Stefansson & M. Novotny, Anal. Chem. 1994, 66, 3466–3471.
Y. Rawjee, and Gy. Vigh, A Peak Resolution Model for the Capillary Electrophoretic Separation of the Enantiomers of Weak Acids with Hydroxypropyl β–Cyclodextrin–Containing Background Electrolytes, 66 *Anal. Chem.* 619–627 (1994).
Y. Rawjee, R. Williams, and Gy. Vigh, Capillary Electrophoretic Chiral Separations Using Cyclodextrin Additives, 680 *J. Chromatogr.* 599–607 (1994).
Y. Rawjee, D. Staerk, and Gy. Vigh, Capillary Electrophoretic Chiral Separations With Cyclodextrin Additives, 635 *J. Chromatogr.*, 291–306 (1993).
Y. Rawjee, R. Williams, and Gy. Vigh, Capillary Electrophoretic Chiral Separations Using β–Cyclodextrin as Resolving Agent, 652 *J. Chromatogr.*, 233–245 (1993).
R. Kuhn, and S. Hoffstetter–Kuhn, Chiral Separation by Capillary Electrphoresis, 34 *Chromatographix* 505–512 (1992).
E. Dose, and G. Guiochon, High–Resolution Modeling of Capillary Zone Electrophoresis and Isotachophoresis, 63 *Anal. Chem.* 1063–1072 (1991).
V. Sustacek, F. Foret, and P. Bocek, Selection of the Background Electrolyte Composition With Respect to Electromigration Dispersion and Detection of Weakly Absorbing Substances in Capillary Zone Electrophoresis, 545 *J. Chromatogr.* 239–248 (1991).
S. Terabe, Electrokinetic Chromatography: An Interface Between Electrophoresis and Chromatography, 8 *Trends in Anal. Chem.* 129–134 (1989).
J. Jorgenson, Zone Electrophoresis in Open–Tubular Capillaries, 3 *Trends in Anal. Chem.* 51–54 (1984).
T. Hirokawa, M. Nishino, N. Aoki, Y. Kiso, Y. Sawamoto, T. Yagi, J–L. Akiyama, Table of Isotachophoretic Indices, 271 *J. Chromatogr.* D1–D10 (1983).
J. Jorgenson and K. Lukacs, Zone Electrophoresis in Open–Tubular Glass Capillaries, 53 *Anal. Chem.* 1298–1302 (1981).

(List continued on next page.)

*Primary Examiner*—Arun S. Phasge
*Assistant Examiner*—Alexander Noguerola
*Attorney, Agent, or Firm*—Baker & Botts, L.L.P.

[57] ABSTRACT

The invention concerns electrophoresis and methods and electrolyte compositions for decoupling or isolating the dual functions of the electrolyte composition in order to increase separation selectivity or reduce electromigration dispersion, or both. An electrolyte composition is used in electrophoresis to separate a charged analyte having a mobility $\mu_a$ in an electric field. The composition includes a buffer system having an ionic component that controls the pH of the composition and mobility matching ions having a mobility $\mu_2$ in the electric field, such that $\mu_a/\mu_2$ equals about one. Alternatively, the buffer system may maintain the composition's pH and a complexing agent may complex with the buffer system to alter the mobility $\mu_2$ of an ionic component of the buffer system, such that $\mu_a/\mu_2$ equals about one. The pH of the composition is within a pH range selected based on the analyte to be separated, and $\mu_2$ remains substantially constant over this pH range.

45 Claims, 19 Drawing Sheets

OTHER PUBLICATIONS

F. Mikkers, F. Everarts, and T. Verheggen, Concentration Distributions in Free Zone Electrophoresis, 169 *J. Chromatogr.* 1–10 (1979).

F. Everaerts, J. Beckers and T. Verheggen, Isotachophoresis Theory, Instrumentation and Applications, 6 *J. Chromatgr.* 27–40 (1976).

E. Dismukes and R. Alberty, Weak Electrolyte Moving Boundary Systems Analogous to the Electrophoresis of a Single Protein, 76 *J. Amer. Chem. Soc.*, 191–197 (1954).

R. Alberty, Moving Boundary Systems Formed By Weak Electrolytes. Theory of Simple Systems Formed by Weak Acids and Bases, 72 *J. Amer. Chem. Soc.*, 2361–2374 (1950).

V. Dole, A Theory of Moving Boundary Systems Formed by Strong Electrolytes, 67 *J. Amer. Chem. Soc.*, 1119–1126 (1945).

INCREASED EFFICIENCY OF ELECTROPHORETIC SEPARATIONS BY MOBILITY MATCHING

BACKGROUND OF THE INVENTION

1. Field of the Invention

The invention relates to electrophoretic separations of analytes and more particularly, to a method, an electrolyte composition, and a kit for independently altering the pH and mobility of ionic components of the composition. Further, the invention relates to a method, an electrolyte composition, and a kit for matching the mobility of ionic components of the composition with that of an analyte without altering, i.e., maintaining, the composition's pH.

2. Description of Related Art

Modern electrophoresis is a powerful approach to the separation and analysis of charged analytes, especially biopolymers. Separation is based on different electrophoretic mobilities of the analytes which, in turn, depend on charge densities. Electrophoretic migration may occur either in an open-robe fused silica capillary as in capillary zone electrophoresis (CZE) or in a supporting medium, such as in gel electrophoresis (GE).

Electrophoresis has been used to separate ions on the basis of their differential migration in an electric field. In addition to differences in mobility, the quality of these charge to volume ratio-based separations may also depend on the amount of band broadening the migrating analytes experience. The absolute ionic mobility, $\mu^0$, is defined as the average velocity of an ion per unit of electric field strength at infinite dilution. This absolute ionic mobility is a characteristic constant for every ionic species in a certain solvent and is proportional to the equivalent conductance at zero concentration. The effective mobility of an ionic species is related to the absolute mobility. Corrections are made for influences such as the electrophoretic retardation and the relaxation effect. Thus, the effective mobility of an ionic species depends on several factors such as the ionic radius, solvation, dielectric constant and viscosity of the solvent, shape and charge of the ion, pH, degree of dissociation and temperature. Under certain conditions, band broadening in capillary electrophoresis is caused only by longitudinal diffusion. Generally, however, band broadening is larger than the broadening caused by diffusion alone. This may be due to the combined dispersion effects of injection, local temperature gradients, electroosmosis, and the heterogeneity of the electric field strength inside the capillary, i.e., electromigration dispersion. Of these factors, electromigration dispersion is normally the most important additional band broadening mechanism.

As noted above, electrophoretic separation of two analytes may only occur if the electrophoretic mobilities of the two components ($\mu_{a1}$ and $\mu_{a2}$) are different. Often the term separation selectivity, $\alpha$, which is the ratio of the two electrophoretic mobilities ($\alpha=\mu_{1a}/\mu_{a2}$), is used to characterize the extent of this dissimilarity. The more different the value of $\alpha$ from unity, the easier it is to accomplish the separation. However, maximization of separation selectivity alone does not guarantee success in electrophoretic separations. An analyst should ensure that the bands of separated analytes remain narrow and do not mix with each other. The ability of the system to maintain narrow bands is characterized by the term separation efficiency. Separation efficiency may be limited only by the diffusive mixing, e.g., natural mixing due to concentration gradients in the separated bands. However, if the effective electrophoretic mobilities of the components of the electrolyte composition are significantly different from those of the analyte and the transfer number of the analytes is much larger than zero, an additional efficiency loss, brought about by electromigration dispersion (or mobility mismatch), may occur due to the distortion of the homogeneity of the electric field in the separation medium. Even mild electromigration dispersion may denigrate the separation.

The effects of electromigration dispersion may be minimized by using an electrolyte composition in which the transfer number of the analyte is about zero. However, due to insufficient detection sensitivity, this is often difficult or impossible to achieve. Another approach is to select buffers whose mobility closely matches the mobilities of the analytes. However, this approach also may fail because the mobility of the analytes and the buffer components vary to different degrees as the composition of the electrolyte composition is changed, e.g., as its pH is changed, or as additional secondary chemical equilibria-inducing agents, such as cyclodextrins, are added. The problem of mobility mismatch is further aggravated by the fact that the secondary chemical equilibria-inducing agents, such as cyclodextrins, may reduce the mobilities of the analytes by as much as 50 to 90%, and buffer components with such low mobilities in all of the useful pH ranges are not available.

SUMMARY OF THE INVENTION

Thus, a need has arisen for a method and an electrolyte composition which permit the maximization of separation efficiency. Further, a need has arisen for such a method and composition which provide matched electrophoretic mobilities for a plurality of analytes and chiral analytes, i.e., analytes not superimposable on their mirror images. These may be accomplished by the decoupling of the pH controlling and mobility matching functions of the electrolyte or by matching the mobility of the analyte, such that the pH of the electrolyte composition remains substantially constant.

In an embodiment of the invention, an electrolyte composition may be used in electrophoresis to separate a charged analyte (or analytes), i.e., an analyte having a positive or negative charge. Such analytes have a mobility $\mu_a$ in an electric field. Such electric fields generally have a strength chosen to avoid arcing, such as less than about 2000 V/cm, and field strength's in a range of about 200 to about 700 V/cm are suitable. The composition includes at least one buffer system, which controls the pH of the composition, and mobility matching ions having a mobility $\mu_2$ in the electric field, such that $\mu_a/\mu_2$ equals about one. Each of these mobilities may have an absolute value less than about $300\times10^{-4}$ cm$^2$/Vs.

A buffer system includes neutral and ionic components. For example, suitable buffer systems include phosphate, acetate, borate, carbonate buffer systems, and the like. Such buffer systems are solutions selected or prepared to minimize changes in the hydrogen ion concentration. The mobility matching ions may be co-ions, i.e., ions having the same charge as the analyte, or counter-ions, i.e., ions having the opposite charge as the analyte.

The pH of the composition may be within the relatively broad pH range of about 2 to about 12. Alternatively, the pH may be within a pH range selected from the group consisting of about 3 to about 5, about 4 to about 6, about 7 to about 9, and about 8 to about 10. It is preferred, however, that the pH selection be within a pH range based on the analyte to be separated. Although electrophoresis may be conducted over relatively broad pH ranges, separation selectivity may be optimized for a particular analyte over relatively narrow pH ranges on the order of about 0.1 pH unit. Nevertheless, because the roles of the controlling pH and mobility matching are decoupled, $\mu_2$ remains substantially constant over pH ranges.

Another embodiment of the invention is a method of electrophoresis to separate a charged analyte. The analyte again has a mobility $\mu_a$ in an electric field, as described above. The method includes the step of providing an electrolyte composition comprised of a buffer system including concentrations of neutral and ionic components and mobility matching ions having a mobility $\mu_2$ in the electric field. This composition again has a pH, which may fall within the ranges described above. The pH is altered by adjusting the concentration ratios of the neutral and ionic components of the buffer system, but the mobility $\mu_2$ of the mobility matching ion remains substantially constant. Similarly, the mobility $\mu_2$ of the matching ions is altered, such that pH remains substantially constant and $\mu_a/\mu_2$ equals about one. The analyte then may be electrophoresed in the composition.

Still another embodiment of the invention is an electrolyte composition for use in electrophoresis to separate a charged analyte having a mobility $\mu_a$ in an electric field. The composition has a predetermined pH and comprises at least one buffer system including at least one ionic component having a mobility $\mu_2$ in the electric field, for maintaining pH. Moreover, it includes at least one complexing agent which complexes with the at least one buffer system to alter the mobility $\mu_2$, such that $\mu_a/\mu_2$ equals about one. Once again, the pH of the composition may fall within the pH ranges described above.

In yet another embodiment, the invention is a method of electrophoresis to separate a charged analyte having a mobility $\mu_a$ in an electric field. The method includes the step of providing an electrolyte composition comprising at least one buffer system for maintaining the pH, which includes at least one ionic component having a mobility $\mu_2$ in the electric field. At least one complexing agent is added to the composition, which complexes with the at least one buffer system to alter the mobility $\mu_2$, such that $\mu_a/\mu_2$ equals about one. The analyte is then electrophoresed in the composition.

Further, in other embodiments, the invention is an electrophoresis kit for separating a charged analyte in an electric field. The kit may comprise at least one buffer system component selected from the group consisting of weak acids and weak bases and a plurality of mobility matching components selected from the group consisting of strong acids and strong bases or their salts. Strong acids and bases completely dissociate in an aqueous solution, i.e., their dissociation constants are greater than about $10^{-3}$. Weak acids and bases, however, do not dissociate completely. Alternatively, the electrophoresis kit may comprise at least one buffer system component selected from the group consisting of weak acids and weak bases and having a mobility in the electric field and at least one complexing agent components to vary the mobility of the buffer system component.

It is a technical advantage of this invention that an analyst may decouple the task of pH buffering from the task of mobility matching in electrophoretic separation. It is also a technical advantage that separation selectivity, which is determined by the components and pH of the electrolyte composition may be optimized without adversely affecting separation efficiency, i.e., the reduction in electromigration dispersion, which is achieved through mobility matching. Similarly, separation efficiency may be optimized without adversely affecting separation selectivity. Another technical advantage of this invention is that an analyst may dynamically adjust the mobility of an ionic component of a buffer system, e.g., a co-ion or counter-ion, to match the analyte mobility in an electrophoretic separation. Thus, separation selectivity may be optimized first by altering the pH of the electrolyte composition. The separation efficiency may then be optimized by adding a complexing agent to change the mobility of the buffer system component.

Moreover, the sensitivity limitations of the detectors currently found in commercial capillary electrophoretic instruments often require the use of analyte concentrations which are high enough to distort the homogeneity of the electric field in the analyte zone and may lead to electromigration dispersion and loss of separation efficiency. The processes and compositions described herein permit the reduction or elimination of electromigration dispersion, the realization of the separation capabilities of this method.

Other objects, advantages, and features will be apparent when the detailed description and the drawings are considered.

BRIEF DESCRIPTION OF THE DRAWINGS

For a more complete understanding of the present invention and the technical advantages thereof, reference is made to the following description taken in conjunction with accompanying drawings, in which.

DETAILED DESCRIPTION OF THE INVENTION

Figure 1:
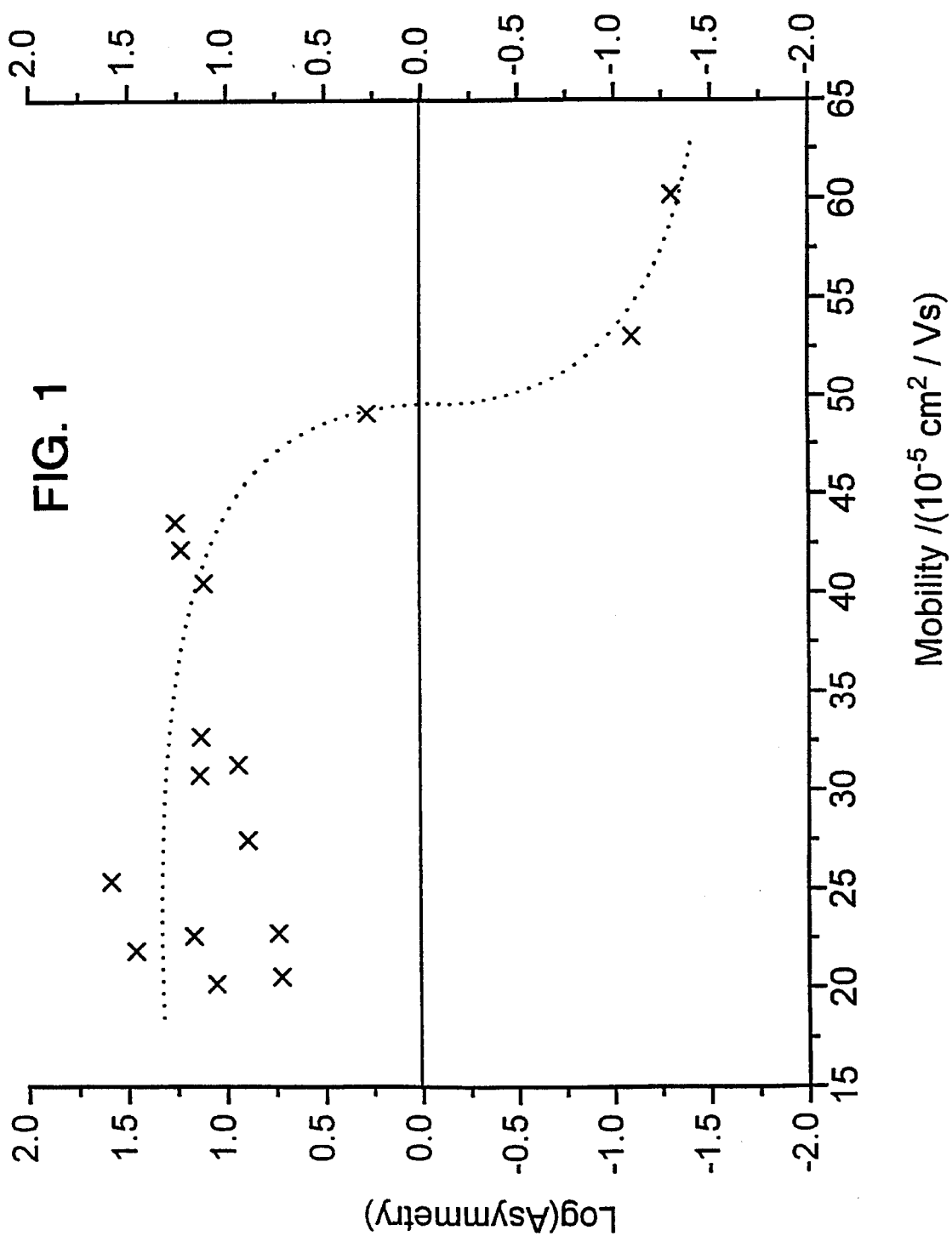
FIG. 1 depicts the logarithm of peak asymmetry as a function of the mobilities of analytes in the electrolyte composition containing tetramethylammonium ion at a pH of about 2.2.

Peak broadening due to electromigration dispersion, which is expressed as peak variance, $\sigma_E^2$, is related to the local electric field strength disparities in the migrating analyte zone and the pure electrolyte composition. In the absence of electroosmotic, flow variances caused by electromigration, dispersion may be expressed in terms of the effective dispersion coefficient, ($D_E$), as follows:

$$\sigma_E^2 = 2D_E t, \quad (1)$$

and may be related to the electric field strength, E(x), as follows:

$$\sigma_E^2 = \frac{2D_E x}{\mu E(x)}. \quad (2)$$

In Equation (2), x is the distance that the analyte has travelled in the electrolyte composition in time t, and μ is its mobility. Therefore, the variance due to electromigration dispersion depends on how E(x) varies over the length of the capillary.

In electrophoretic separation, Ohm's law relates the potential gradient, dV/dx; the current, i; and the specific conductance, κ. The relationship may be expressed as follows:

$$\frac{dV}{dx} = -\frac{i}{\kappa}. \quad (3)$$

In addition, the conductance is related to the mobilities ($\mu_k$) and the concentrations ($C_k$) of the individual ions within the electrolyte composition. This relationship may be described as follows:

$$\kappa = \sum_{k=1}^{n} F|z_k|\mu_k C_k. \quad (4)$$

In Equation (4), F is the Faraday constant, and $Z_k$ is the charge of the kth ion. Therefore, the combination of Equations (3) and (4) indicates that current is related to the concentration and mobility of the ions, and the potential gradient along the separation chamber as follows:

$$i = -F \sum_{k=1}^{n} z_k \mu_k C_k \frac{dV}{dx}. \quad (5)$$

If the separation chamber is filled with a homogeneous electrolyte composition, $X^+Y^-$, if the analyte has the same ionic charge as co-ion $X^+$, and if the electrophoretic separation is adequately thermostatted and operated within the linear region of Ohm's law, then, according to Kohlrausch's regulating function of independent ion migration, the sums of the equivalent concentrations within the analyte and electrolyte composition zones may be equated as follows:

$$\omega^B = \sum_{k=1}^{n} \frac{C_k^B}{r_k} = \omega^S = \sum_{k=1}^{n} \frac{C_k^S}{r_k}. \quad (6)$$

In Equation (6), $C_k^B$ represents the molar concentration of constituent k of the electrolyte composition, and $r_k$ is its ionic mobility relative to the mobility of a reference constituent. Moreover, the mobility of the electrolyte composition co-ion $X^+$ is used as the reference mobility. If the ions involved are monovalent and are derived from strong electrolytes, i.e., strong acids or bases, Kohlrausch's regulating function becomes:

$$\omega^S = \frac{C_{A^+}^S}{r_{A^+}} + \frac{C_{X^+}^S}{r_{X^+}} + \frac{C_{Y^-}^S}{r_{Y^-}} = \omega^B = \frac{C_{X^+}^B}{r_{X^+}} + \frac{C_{Y^-}^B}{r_{Y^-}} \quad (7)$$

In view of the condition of electroneutrality and by the combination of like-terms, Equation (7) may be further reduced to yield the following:

$$\omega^S = C_{X^+}^S \left(1 + \frac{1}{r_{Y^-}}\right) + C_{A^+}^S \left(\frac{1}{r_{A^+}} + \frac{1}{r_{Y^-}}\right) \quad (8)$$

$$\omega^B = C_{X^+}^B \left(1 + \frac{1}{r_{Y^-}}\right). \quad (9)$$

By equating Equations (8) and (9) and simplifying, the resulting equation is as follows:

$$C_{X+}^B = C_{X+}^S + C_{A+}^S \left[ \frac{r_{A+} + r_{Y-}}{1 + r_{Y-}} \right] \left[ \frac{1}{r_{A+}} \right] \quad (10)$$

Applying the requirement of electroneutrality and Ohm's law, the effect of a analyte component upon the local electric field strength may be obtained as follows:

$$\frac{E^B}{E^S(x,t)} = 1 - \left[ \frac{C_{A+}^S(x,t)}{C_{X+}^B} \frac{(r_{A+} + r_{Y-})(1 - r_{A+})}{(1 + r_{Y-})r_{A+}} \right] \quad (11)$$

Equation (11) relates the electric field strengths in the analyte zone and in the electrolyte composition zone. The local electric field within the analyte zone may be maintained at the same strength as in the electrolyte composition zone by reducing the second term on the right hand side of Equation (11) to zero. This may be accomplished in one of at least four methods. First, the concentration of the analyte component, $C_{A+}^S(x,t)$, may be kept very small with respect to the concentration of the electrolyte composition co-ion, $C_{X+}^B$. Second, the concentration of the electrolyte composition co-ion, $C_{X+}^B$, may be made very large with respect to the concentration of the analyte component, $C_{A+}^S(x,t)$. Third, the mobility of the analyte, $\mu_{A+}$, may be made about equal to the mobility of the electrolyte composition co-ion, $\mu_x$. Thus, $r_{A+}$, may be made equal to one. Fourth, the mobility ratio of the analyte, $r_{A+}$, may be made equal to the mobility ratio of the counter-ion, $r_{Y-}$, or the mobility of the analyte, $\mu_{A+}$, can made to be equal, but opposite in sign to that of the counter ion $\mu_{Y-}$.

When no localized disruption of the electric field occurs, a Gaussian peak is observed, and no peak distortion due to electromigration dispersion occurs. When the mobility ratio of the sample analyte to that of the electrolyte composition co-ion is greater than unity, then the electric field strength in the analyte zone may be less than in the pure electrolyte composition zone. A stable trailing edge and a diffuse leading edge is maintained in the sample zone. This concentration profile results in detection of an asymmetric peak with a long convex front. Conversely, when the mobility of the analyte is less than that of the electrolyte composition co-ion, i.e., its mobility ratio is less than unity, the electric field strength in the analyte zone is greater than in the pure electrolyte composition zone. The stable boundary is maintained on the leading edge of the analyte zone, and an asymmetric peak with a long concave tail is detected.

According to the invention, the equalization of the local electric field in the analyte zone and in the pure electrolyte composition zone, i.e., mobility matching, may be achieved in at least two ways. First, equalization may be achieved by decoupling the dual roles of the electrolyte composition, i.e., the control of the pH and the matching of the mobility of the analyte, and reallocating one of these roles, e.g., pH control, solely to the counter-ion and the other role, e.g., mobility matching, to the co-ion. The pH of the electrolyte composition then may be controlled without regard to its mobility to maximize the separation selectivity. The mobility of the co-ion may be adjusted without regard to the pH value to equalize the local electric field strength in the analyte zone and in the pure electrolyte composition zone.

Such a division of the roles of the electrolyte composition may be achieved when (a) the co-ion is a permanent ion, such as an ion derived from a strong acid or strong base, and the counter-ion is a conjugate acid cation or conjugate base anion, such as those derived from a weak base or from a weak acid, or (b) the counter-ion is a permanent ion, such as an ion derived from a strong acid or strong base, and the co-ion is a conjugate acid cation or conjugate base anion, such as those derived from a weak base or from a weak acid.

Specifically, if the buffering function in the electrolyte composition is allocated solely to the counter-ion, which is derived from a weak electrolyte, its mobility may vary freely. The local electric field equalization function, i.e., mobility matching function, then is allocated solely to the co-ion, which is derived from a strong electrolyte and selected from a family of ions whose mobility covers a broad range, but whose mobility remains constant as the pH of the electrolyte composition is altered.

When the counter-ion yielding weak electrolyte buffer is a weak acid, the co-ion yielding strong electrolyte must be a strong base, e.g., an alkali hydroxide, an alkaline earth hydroxide, or a quaternary ammonium hydroxide type compound. The electrolyte composition is prepared by dissolving the weak acid buffer component at the desired concentration, followed by the addition of the local electric field equalizing, i.e., mobility matching, strong base in increasing quantities until the electrolyte composition attains the pH desired for optimal separation selectivity of the analyte.

After the electrophoretic separation of the analyte is completed with this electrolyte composition, the shape of the analyte peak is determined. If the analyte peak is asymmetric, another strong base of higher ionic mobility (for fronting analyte peaks) or lower ionic mobility (for tailing analyte peaks) may be selected to make the next electrolyte composition of similar pH and ionic strength, but of different co-ion mobility. This selection is aided by the Fergusson plot of the co-ion. The procedure is repeated until the analyte peak becomes symmetric. When the counter-ion yielding weak electrolyte is a weak base, the co-ion yielding strong electrolyte must be a strong acid, e.g., a sulfonic acid. The electrolyte composition then may be prepared by the same procedure described above, and the procedure is repeated with a new strong acid until a symmetric analyte peak is obtained.

In addition, the buffering function can be allocated to the co-ion which is derived from a weak electrolyte, whose mobility may vary freely. The local electric field equalizing function, i.e., mobility matching function, is then allocated to the counter-ion, which is derived from a strong electrolyte, whose mobility does not vary with the changing pH.

Increased separation efficiency according to this role decoupling method depends on the availability of a series of cationic and anionic strong electrolytes, whose pH-independent mobility spans the electrophoretically useful range. Selection of these components can be aided by their Fergusson plots determined at constant, finite ionic strengths.

The mobility matching ions may be selected from the group consisting of quaternary ammonium moieties, sulfonate moieties, and sulfate moieties. For example, the matching ions may be selected from the group of acids consisting of $RSO_3H$ and $RSO_4H$, wherein R is a moiety selected from the group consisting of alkyls, alkylenes, substituted alkyls, aryls, substituted aryls, cycloalkyls, substituted cycloalkyls, polyoxyethylenes, polyoxyalkylenes, and polysaccharides. Alternatively, the matching ions may be selected from the group of bases consisting $(R_1)(R_2)(R_3)(R_4)NOH$, $(R_1)(R_2)(Cycl_1)NOH$, and $(R_1)(Cycl_2)NOH$, wherein $R_1$, $R_2$, $R_3$, and $R_4$ are selected from the group of moieties consisting of alkyls, substituted alkyls, aryls, substituted aryls, cycloalkyls, substituted cycloalkyls, polyoxyethylenes, polyoxyalkylenes, and polysaccharides; $Cycl_1$ is a structure with two bonds to N; and $Cycl_2$ is a structure with three bonds to N.

Thus, the matching ions may have a charge of the same or the opposite sign of the analyte. For example, when the analyte is an anion, the buffer system may be a conjugate acid buffer system, and the matching ions will have a charge of the same sign as the analyte. Alternatively, the buffer system may be a conjugate base buffer system, and the matching ions will have a charge of the opposite sign as the analyte. Suitable anions include sulfates, sulfonates, phosphates, phosphonates, borates, carboxylates, phenolates, and the like. If, however, the analyte is a cation, the buffer system may be a conjugate base buffer system, and the matching ions will have a charge of the same sign as the analyte. Alternatively, the buffer system may be a conjugate acid buffer system, and the matching ions will have a charge of the opposite sign as the analyte. Suitable cations include primary, secondary, tertiary, and quaternary amines and the like.

According to a second method for increasing separation efficiency, an electrolyte composition may be prepared which includes a buffer system and a complexing agent which may complex with both the dissociated and nondissociated forms of the buffer system and alter its effective electrophoretic mobility. The effective mobility of the complexed ionic component will depend on the mobility of both of its free and complexed forms, the analytical concentration of the ionic component in the electrolyte composition, the hydronium ion concentration of the electrolyte composition, and the analytical concentration of the complexing agent in the electrolyte composition. By keeping any two of these variables constant, for example, the concentration of the complexing agent and the pH, and varying the third, the mobility of the ionic component may be continuously tuned. Thus, the local electric field strengths in the analyte zone and in the pure electrolyte composition zones may be equalized, and the electromigration dispersion can be reduced or eliminated.

Suitable complexing agents include oligosaccharides and in particular, those selected from the group consisting of linear, branched, and cyclic oligosaccharides with a degree of polymerization greater than three, and derivatives thereof. Such derivatives may include O-derivatives and des-O-derivatives. Alternatively, the complexing agent may be selected from the group consisting of maltoses which also have a degree of polymerization greater than three, and derivatives thereof. Again, such derivatives may include O-derivatives and des-O-derivatives. It is preferred, however, that such oligosaccharides and maltoses have degrees of polymerization greater than six. Further, the complexing agent may be selected from the group consisting of cyclomaltohexaoses, cyclomaltoheptaoses, cyclomaltooctaoses, and derivatives thereof. These derivatives again may include, but are not limited to, O-derivatives and des-O-derivatives.

The following examples are shown as possible implementations of the invention, but it should be understood that these examples are intended to be only illustrations, and should not be construed as exclusive embodiments. Each of these examples was performed using the same apparatus. A P/ACE 2100 capillary electrophoresis system, such as those manufactured by Beckman Instruments, Inc., Fullerton, Calif., was used for the experiments, with its UV detector set at about 210 nm. Untreated, 25-µm-i.d., 150 µm-o.d. fused silica capillaries, such as those manufactured by Polymicro Technologies, Phoenix, Ariz., were used for the mobility and complexation constant determinations (about 40 cm from injector to detector, about 47 cm total length). The temperature of the thermostatting fluid was maintained at about 37° C. The field strength was varied between about 150 and 750 V/cm in order to keep power dissipation in the about 80 to 100 mW range. The analyte was injected electrokinetically. The electroosmotic flow was measured by injecting a dilute solution of benzyl alcohol.

EXAMPLE I

A series of electrophoretic mobility measurements were completed using electrolyte compositions which contained about 50 mM reagent grade phosphoric acid as buffer constituent. The pH of the successive compositions was controlled at a pH of about 2.2 with concentrated solutions of tetramethylammonium hydroxide, tetraethylammonium hydroxide, tetrapropylammonium hydroxide, tetrabutylammonium hydroxide, and tetrapentylammonium hydroxide. A test mixture of analytes containing aromatic amine solutes with a broad range of mobilities was injected into each electrolyte composition, and the peak asymmetries of the test analytes were determined. Peak asymmetry was calculated as A=b/a, where a is the time difference between the peak front at about 10% peak height and the peak maximum and b is the time difference between the peak tail at about 10% peak height and the peak maximum.

Figure 2:
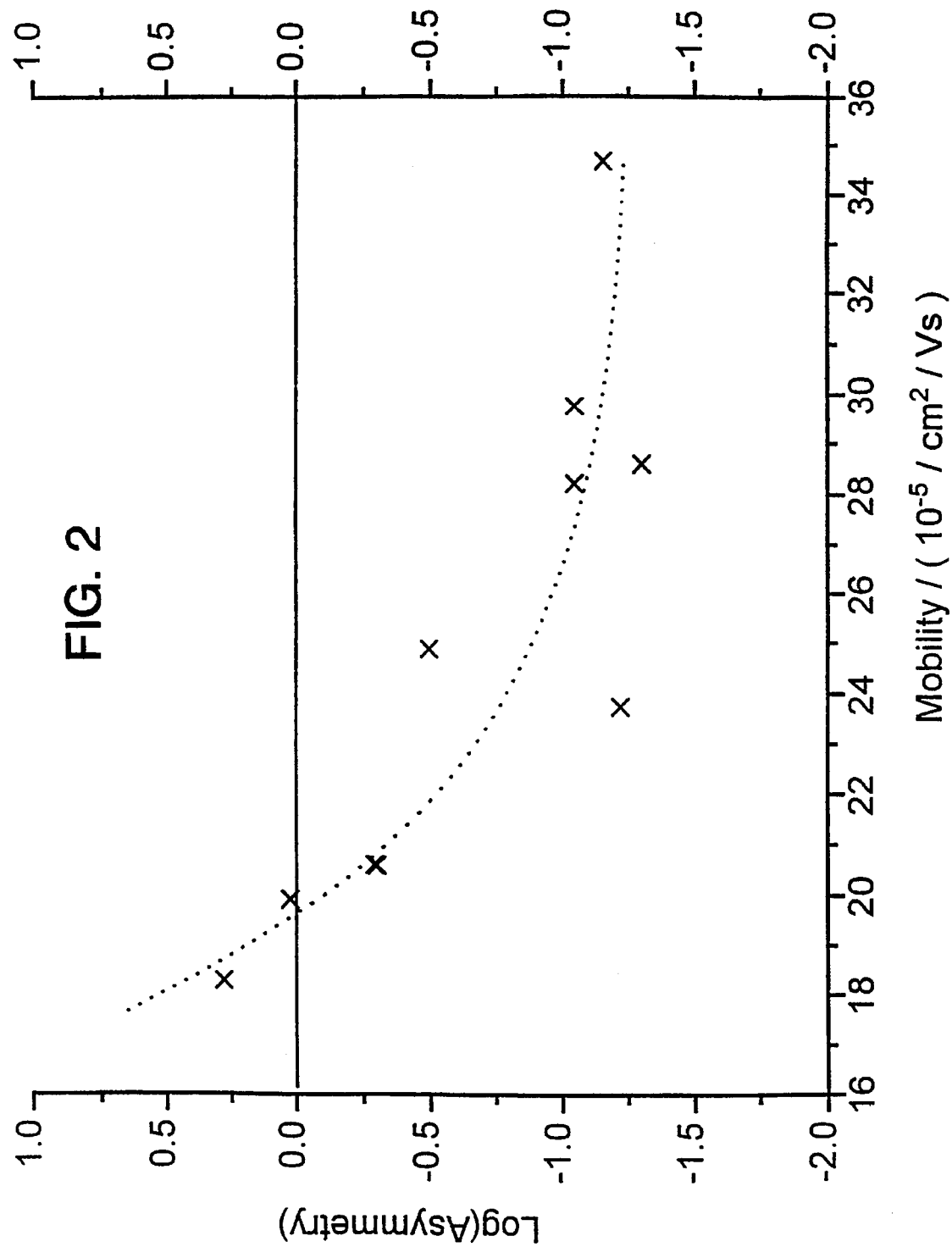
FIG. 2 depicts the logarithm of peak asymmetry as a function of the mobilities of analytes in the electrolyte composition containing tetrabutylammonium ion at a pH of about 2.2.
Figure 3:
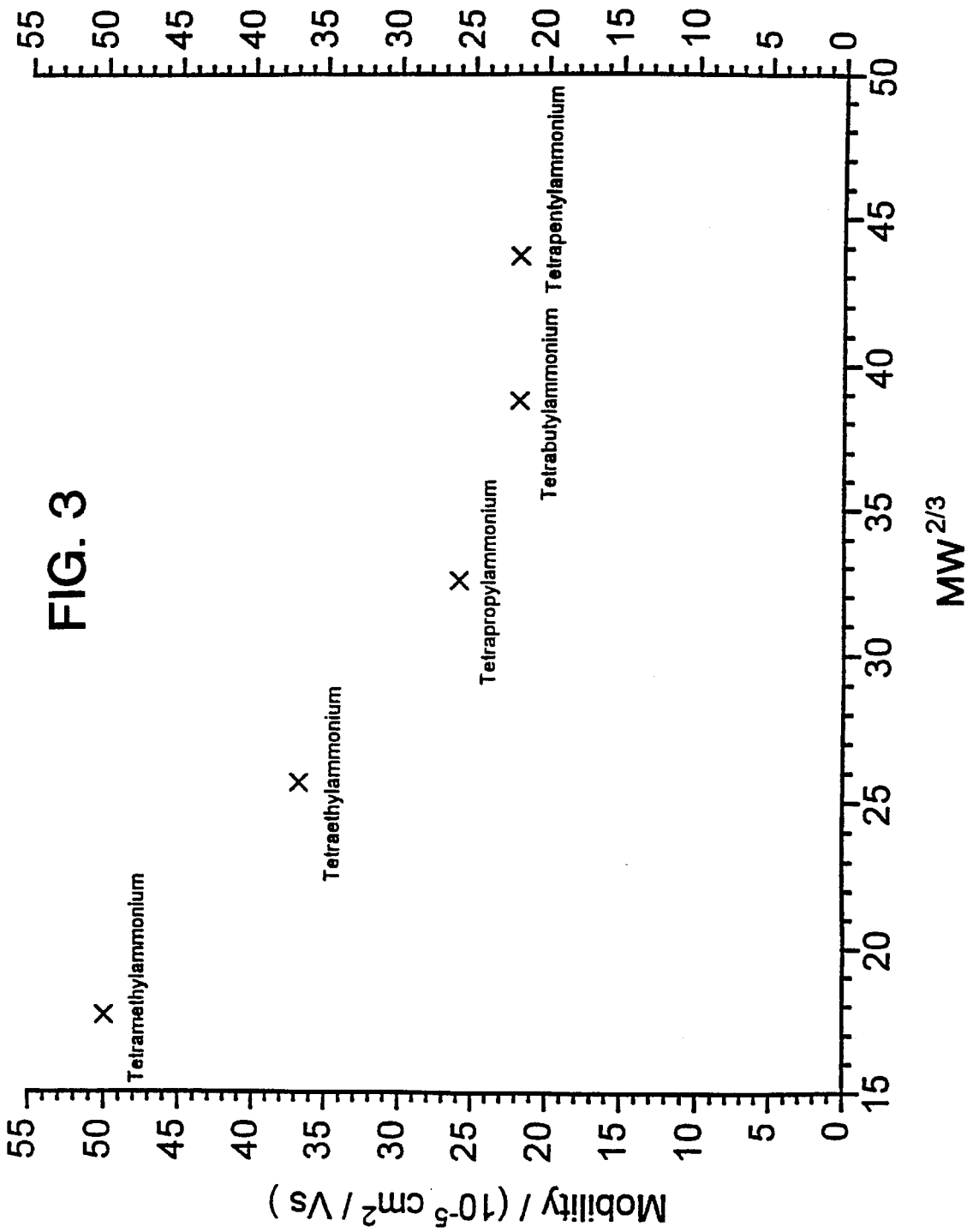
FIG. 3 depicts a Fergusson plot of the tetraalkylammonium ions, i.e., the effective mobilities of the tetraalkylammonium ions as a function of the ⅔rd power of their molecular weight.
Figure 4:
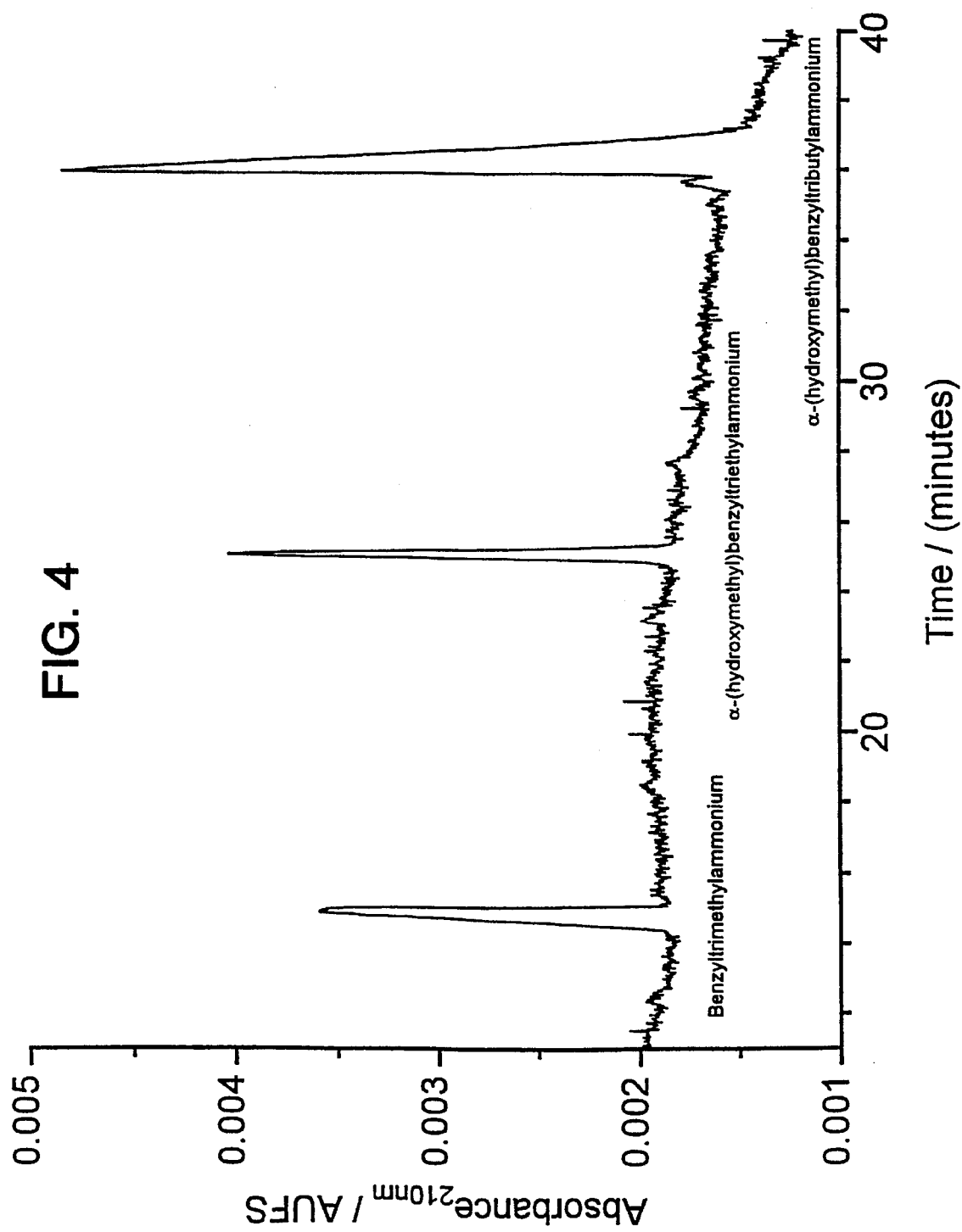
FIG. 4 depicts electrophoretic separation of the analytes benzyltrimethylammonium ion, α-(hydroxymethyl)benzyltriethylammonium ion, and α-(hydroxymethyl)benzyl-tributylammonium ion, using an electrolyte composition including about 50 mM phosphoric acid solution, the pH of which was adjusted to about 2.2 by the addition of tetrapropylammonium hydroxide.

Logarithms of peak asymmetries are depicted in FIG. 1 as a function of the mobilities of the test analytes in the electrolyte composition containing tetramethylammonium ion. In FIG. 2, logarithms of peak asymmetries are depicted as a function of the mobilities of the test analytes in the electrolyte composition containing tetrabutylammonium ion. Analytes with mobilities below about $45 \times 10^{-5}$ cm$^2$/Vs tail in the electrolyte composition containing tetramethylammonium ion. Analytes with mobilities above about $22 \times 10^{-5}$ cm$^2$/Vs front in the electrolyte composition containing tetrabutylammonium ion, while analytes with mobilities below about $22 \times 10^{-5}$ cm$^2$/Vs tail in this composition. The Fergusson plot of the tetraalkylammonium ions, i.e., the effective mobilities of the tetraalkylammonium ions as a function of the ⅔rd power of their molecular weight, depicted in FIG. 3, allows an analyst to select a matching co-ion for a particular separation, without changing either the pH or the ionic strength of the electrolyte composition. The electropherogram of a test sample obtained with tetrabutylammonium cation as the mobility matching ion is depicted in FIG. 4.

EXAMPLE II

A homologous series of dialkyl substituted morpholine compounds were synthesized. 4-alkyl-morpholine was reacted with alkyl iodides of increasing chain length, in refluxing toluene. The quaternary amine formed was not soluble in toluene and precipitated as a light solid. The precipitate was removed by vacuum filtration, washed with toluene, and vacuum dried at about 70° C. in a vacuum of about 68.6 cm of Hg for about 3 hours. Nuclear magnetic resonance analysis was performed on the resultant product and indicated, in all cases, that a pure quaternary ammonium product had been obtained. The halide salt was converted into free base form by passing it through an OH-form anion exchange resin. The N,N-dialkyl morpholine hydroxide solutions were assayed by titrating them with a solution of about 0.2M HCl.

Figure 5:
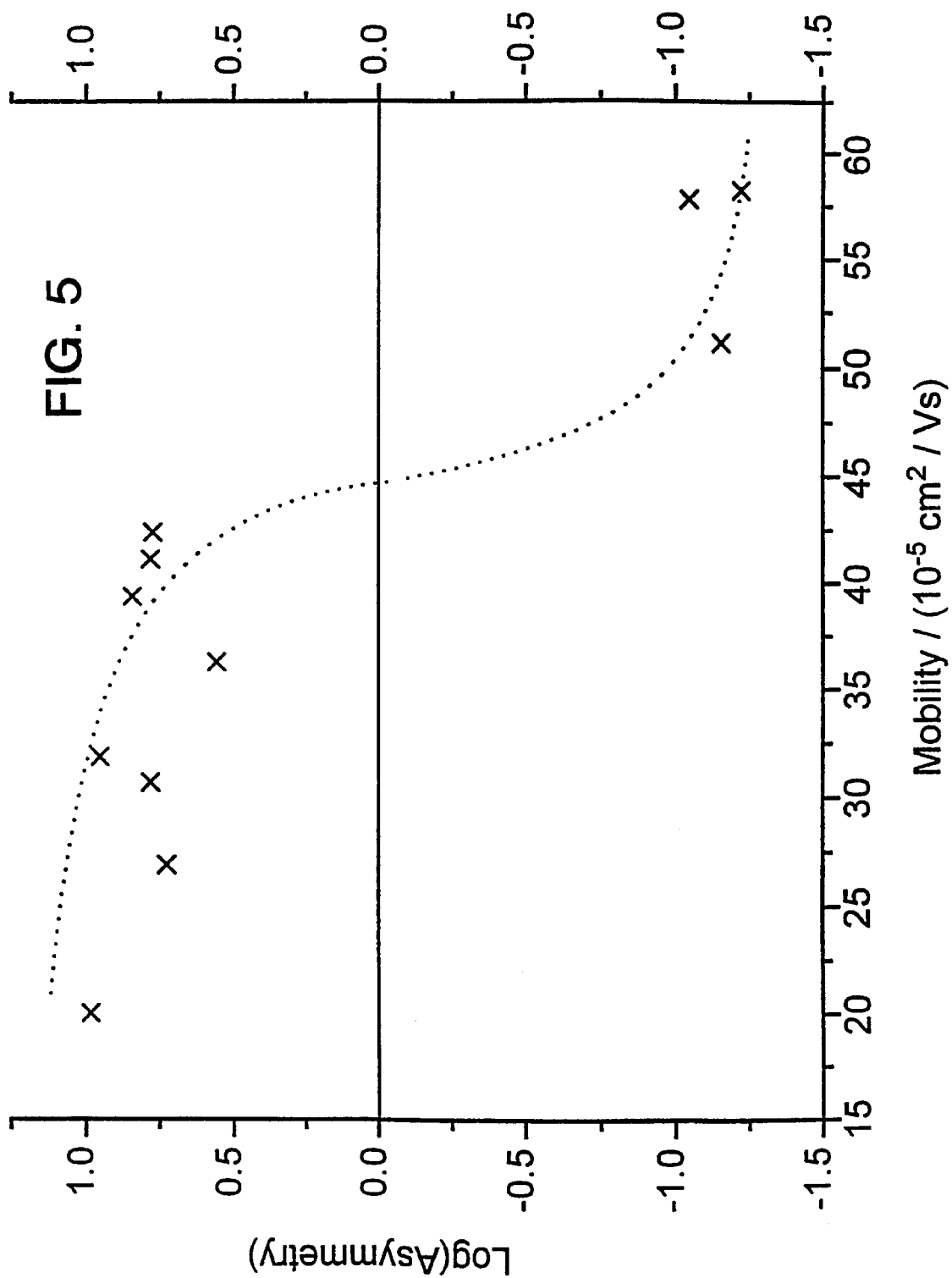
FIG. 5 depicts the logarithm of peak asymmetry as a function of the mobilities of analytes in the electrolyte composition containing N,N-dimethylmorpholine ion at a pH of about 2.2.
Figure 6:
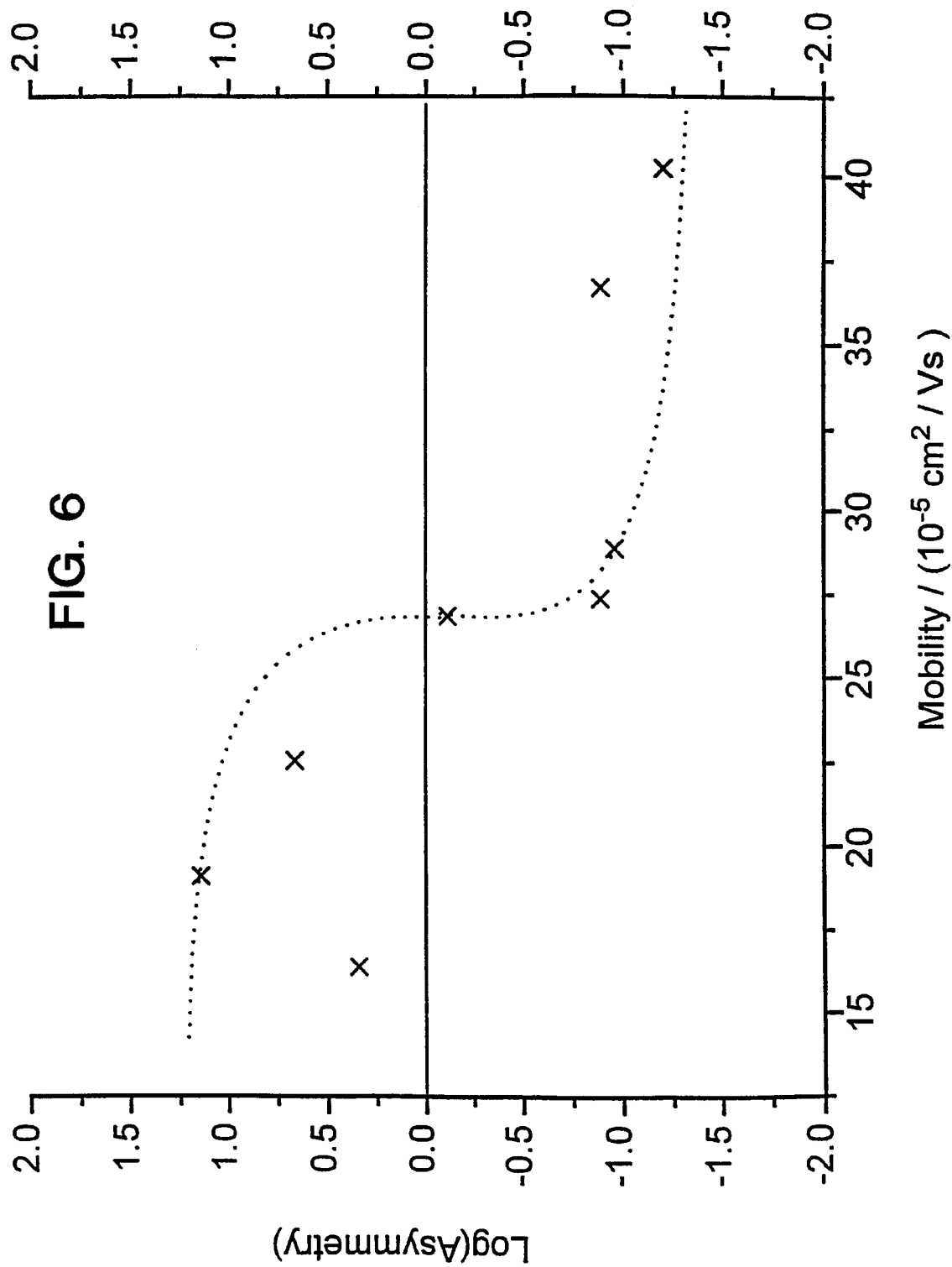
FIG. 6 depicts the logarithm of peak asymmetry as a function of the mobilities of analytes in the electrolyte composition containing N-methyl-N-nonylmorpholine ion at a pH of about 2.2.

A series of electrophoretic mobility measurements were performed using electrolyte compositions which contained about 50 mM reagent grade phosphoric acid as buffer component. The pH of the successive compositions was controlled at a pH of about 2.2 with the assayed solutions of N,N-dialkyl morpholine hydroxides. A test mixture of analytes containing aromatic amine solutes with a broad range of mobilities was injected into each electrolyte composition, and the peak asymmetries of the test compounds were determined. Logarithms of peak asymmetries are depicted in FIG. 5 as a function of the mobilities of the test analytes in the electrolyte composition containing N,N-dimethylmorpholine ion. In FIG. 6, the logarithms of peak asymmetries are depicted as a function of the mobilities of the test analytes in the electrolyte composition containing N-methyl-N-nonylmorpholine ion.

Figure 7:
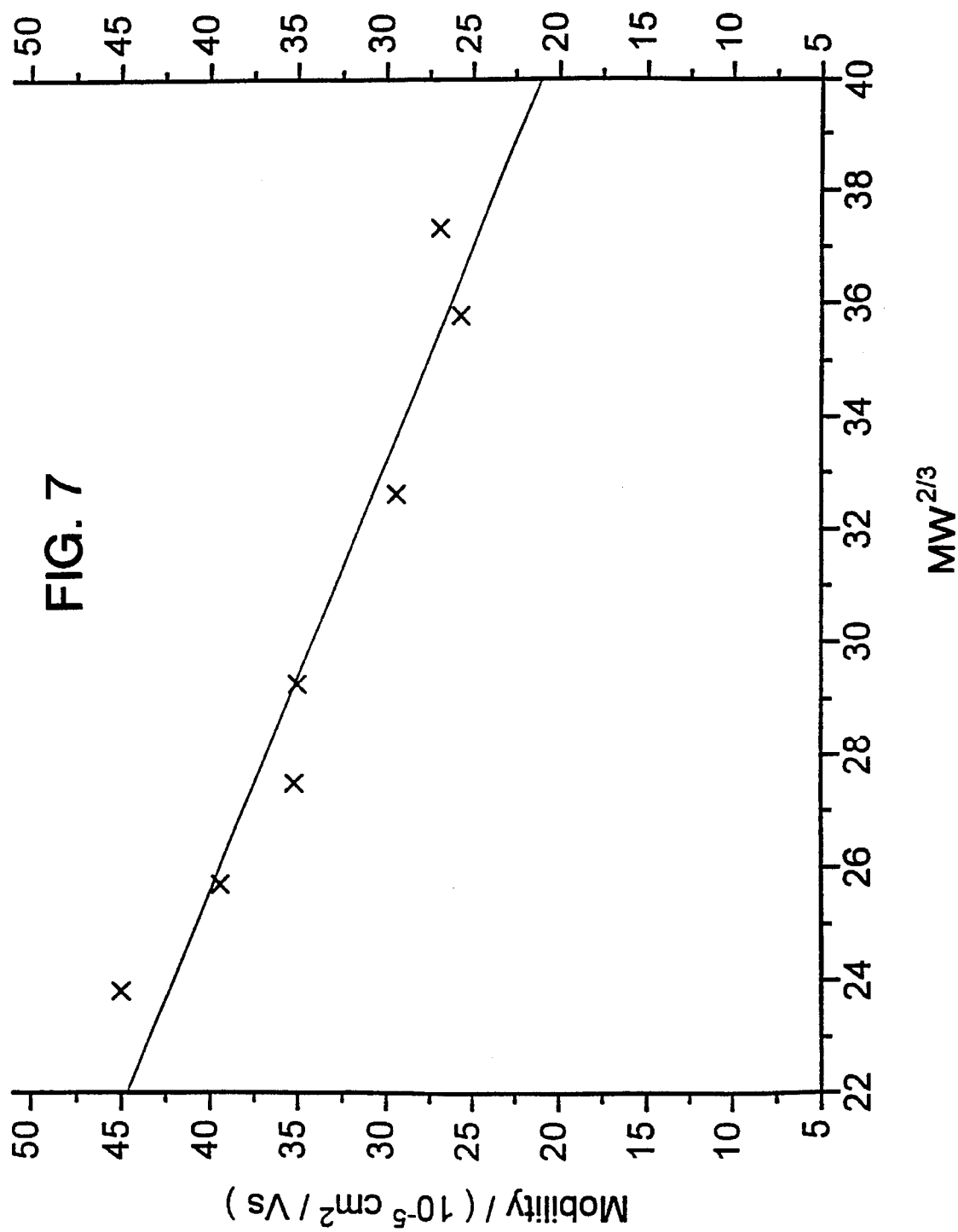
FIG. 7 depicts a Fergusson plot of the N,N-dialkylmorpholine ions, i.e., the effective mobilities of the N,N-dialkylmorpholine ions as a function of the ⅔rd power of their molecular weight.
Figure 8:
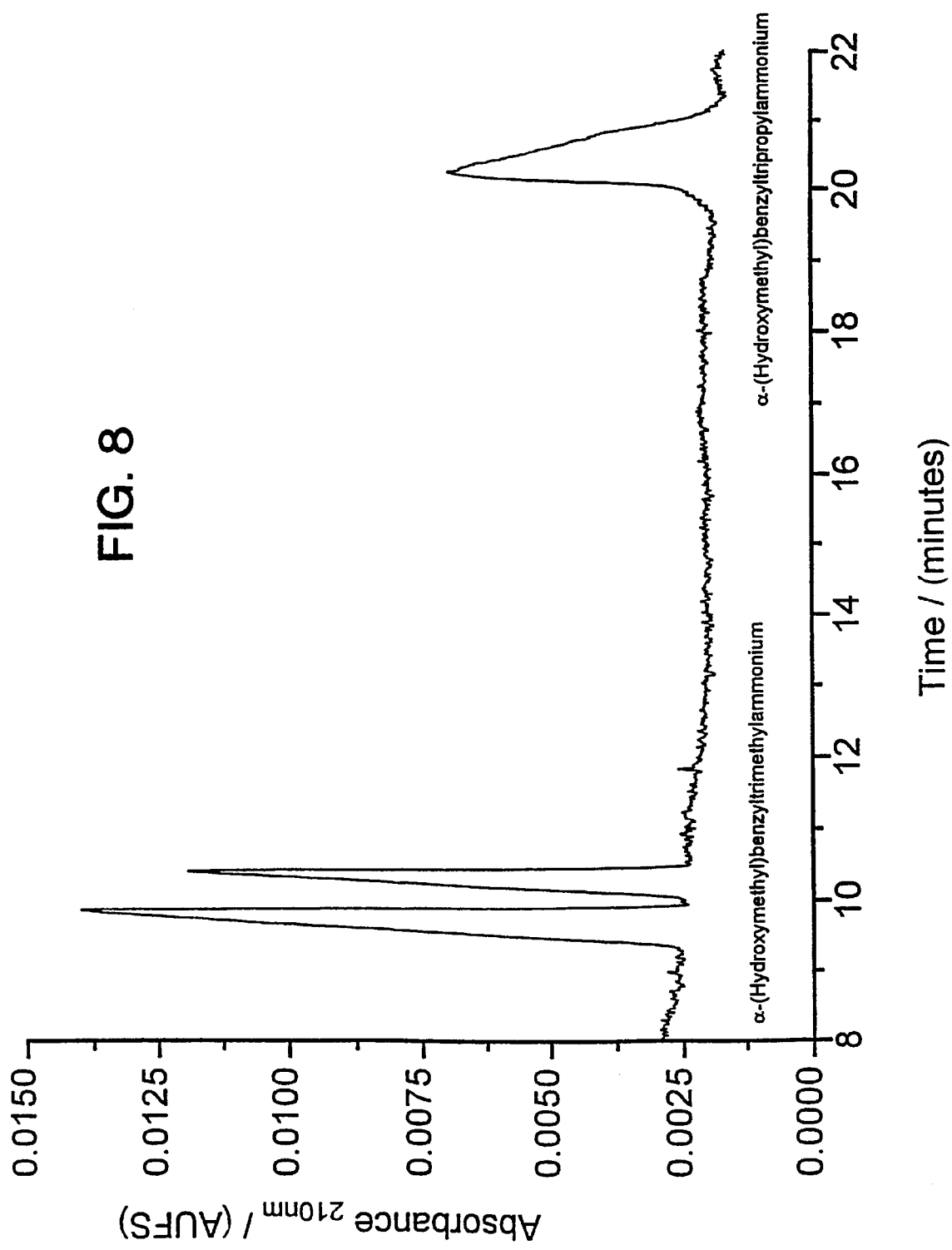
FIG. 8 depicts the electrophoretic separation of the analytes: α-(hydroxymethyl)benzyltrimethylammonium ion and α-(hydroxymethyl)benzyltripropylammonium ion, using an electrolyte composition including about 50 mM phosphoric acid solution, the pH of which was adjusted to about 2.2 by the addition of N-methyl-N-nonylmorpholino hydroxide.

Analytes with mobilities below about $45 \times 10^{-5}$ cm$^2$/Vs tail in the electrolyte composition containing N,N-dimethylmorpholine ion. Analytes with mobilities above about $27 \times 10^{-5}$ cm$^2$/Vs front in the electrolyte composition containing N-methyl-N-nonylmorpholine ion, while analytes with mobilities below about $27 \times 10^{-5}$ cm$^2$/Vs tail in this background electrolyte. The Fergusson plot of the N,N-dialkyl morpholine ions, i.e., the effective mobilities of the N,N-dialkyl morpholine ions as a function of the ⅔rd power of their molecular weight, is depicted in FIG. 7. This plot allows an analyst to select a matching co-ion for a particular separation, without changing either the pH or the ionic strength of the electrolyte composition. The electropherogram of a test analyte obtained with the electrolyte composition that contains the N-methyl-N-nonylmorpholino cation as the mobility matching ion is depicted in FIG. 8.

EXAMPLE III

A homologous series of N-alkyl-N-methoxy(oligoethoxy) morpholine compounds were synthesized. 4-alkyl-morpholine was reacted with methoxy(oligoethoxy) tosylates of increasing mer-number, in refluxing toluene. The quaternary amine formed was not soluble in toluene and precipitated as a light solid, or phase separated as an orange oil. The precipitate was removed by vacuum filtration, washed with toluene, and vacuum dried at about 70° C. in a vacuum of about 68.6 cm of Hg for about 3 hours. The oils were separated from the toluene phase and washed with dichloromethane. Nuclear magnetic resonance analysis was performed on the resultant product and indicated, in all cases, that a quaternary ammonium product had been obtained. The halide salt was converted into free base form by passing it through an OH-form anion exchange resin. The N-alkyl-N-methoxy(oligoethoxy) morpholine hydroxide solutions were assayed by titrating them with a solution of about 0.2M HCl.

Figure 9:
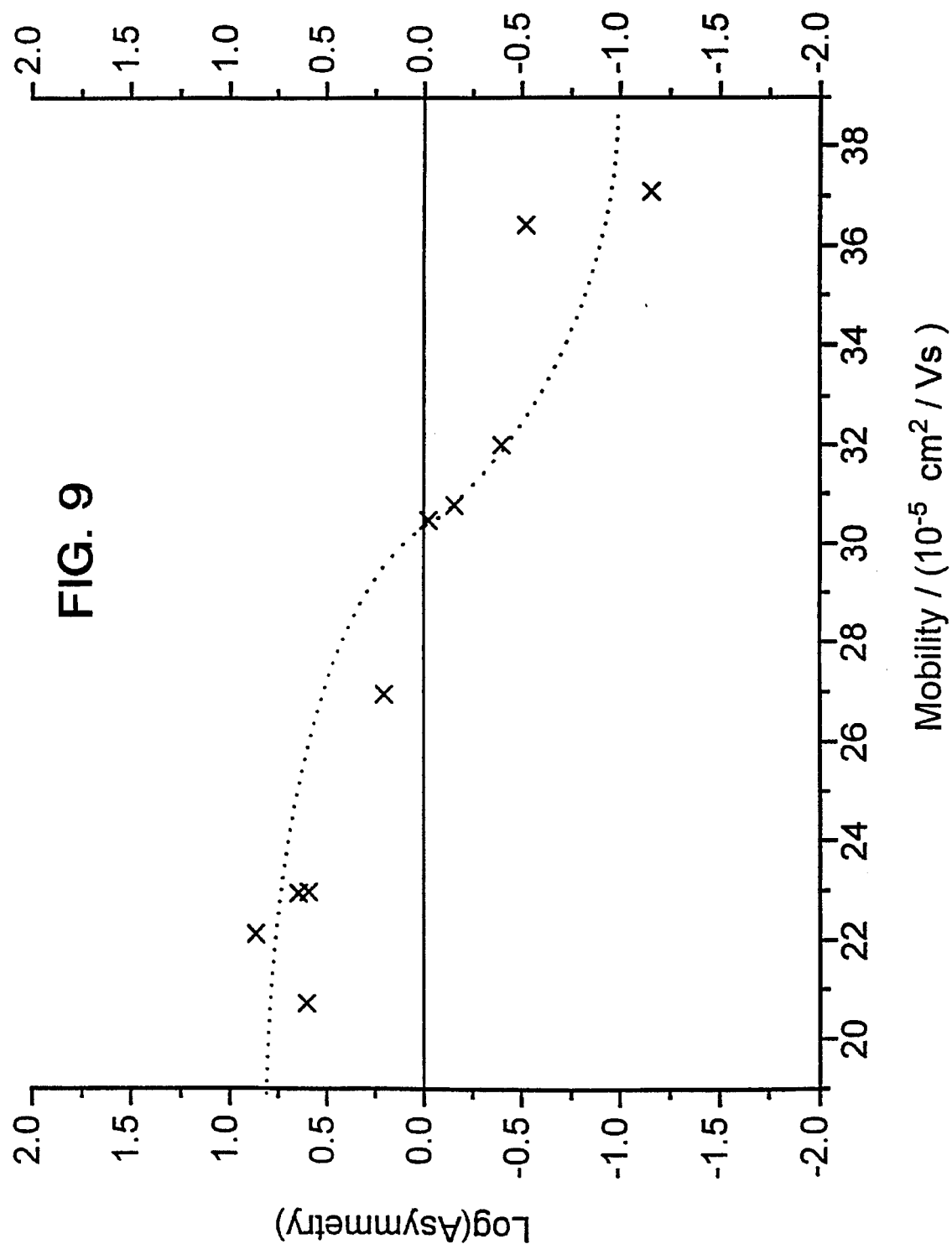
FIG. 9 depicts the logarithm of peak asymmetry as a function of the mobilities of analytes in the electrolyte composition containing N-methyl-N-methoxy(ethoxy)morpholine ion at a pH of about 2.2.
Figure 10:
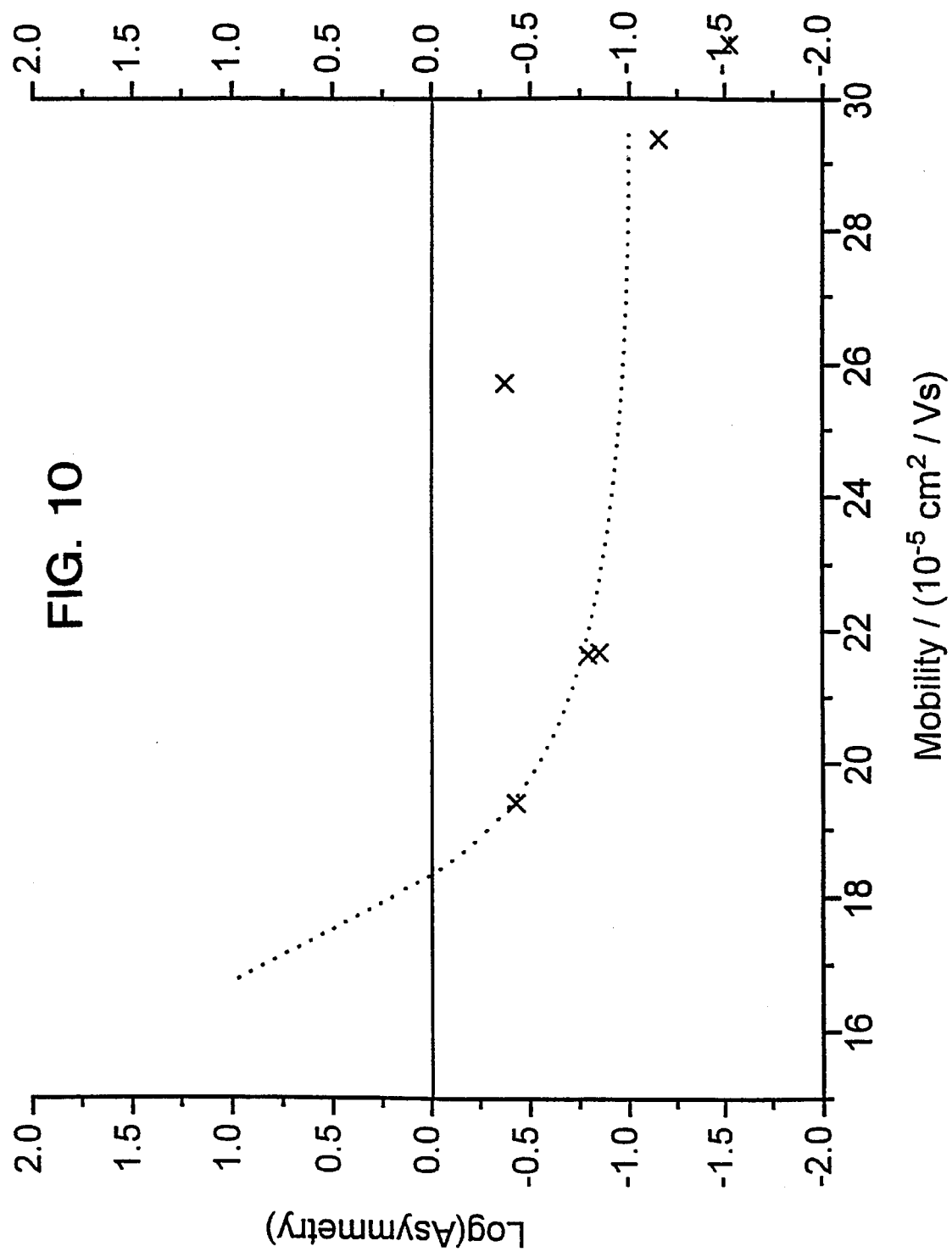
FIG. 10 depicts the logarithm of peak asymmetry as a function of the mobilities of analytes in the electrolyte composition containing N-methyl-N-methoxy(nonaethoxy)morpholine ion at a pH of about 2.2.
Figure 11:
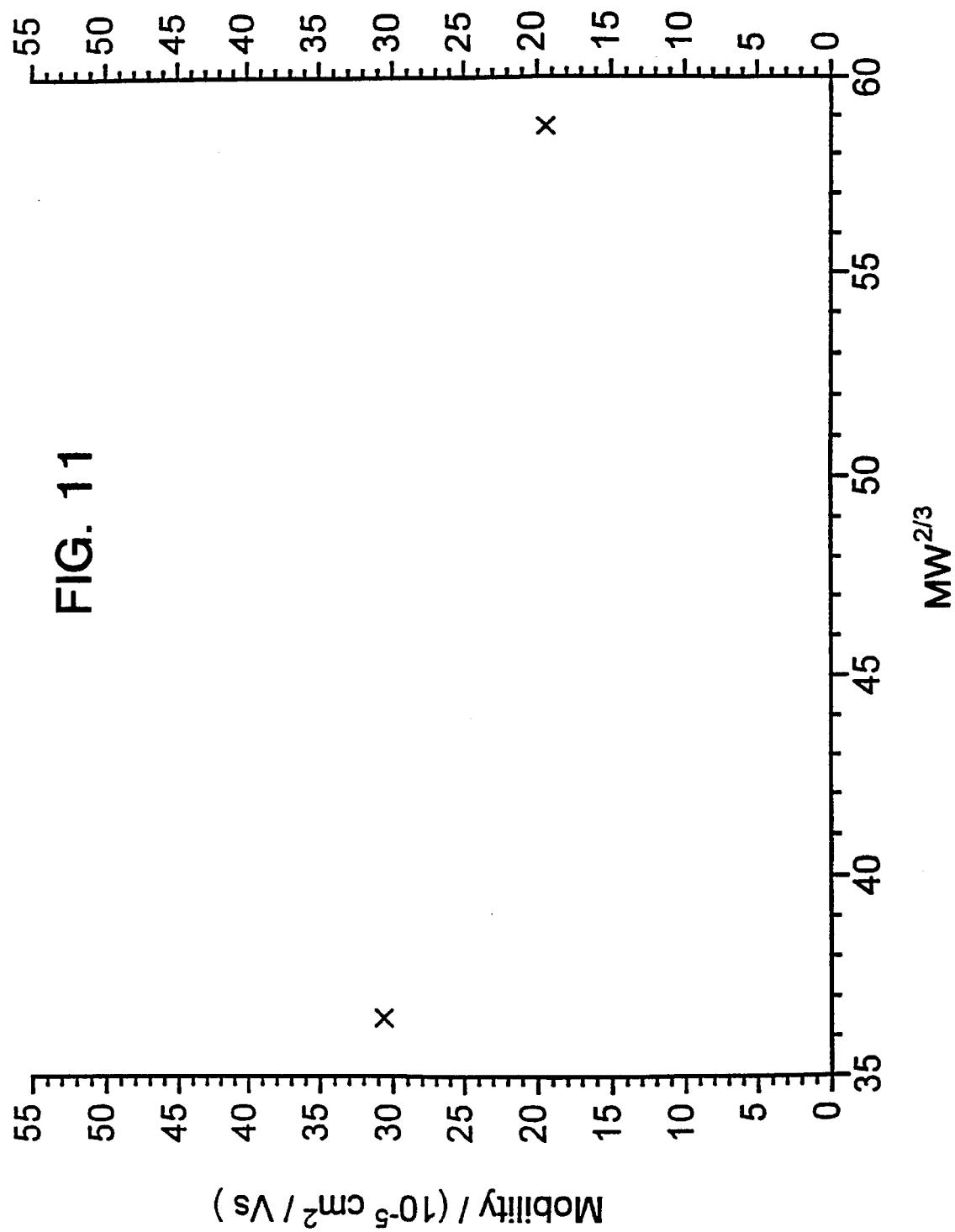
FIG. 11 depicts a Fergusson plot of the N-alkyl-N-methoxy(oligoethoxy)morpholine ions, i.e. the effective mobilities of the N-alkyl-N-methoxy(oligoethoxy)morpholine ions as a function of the ⅔rd power of their molecular weight.
Figure 12:
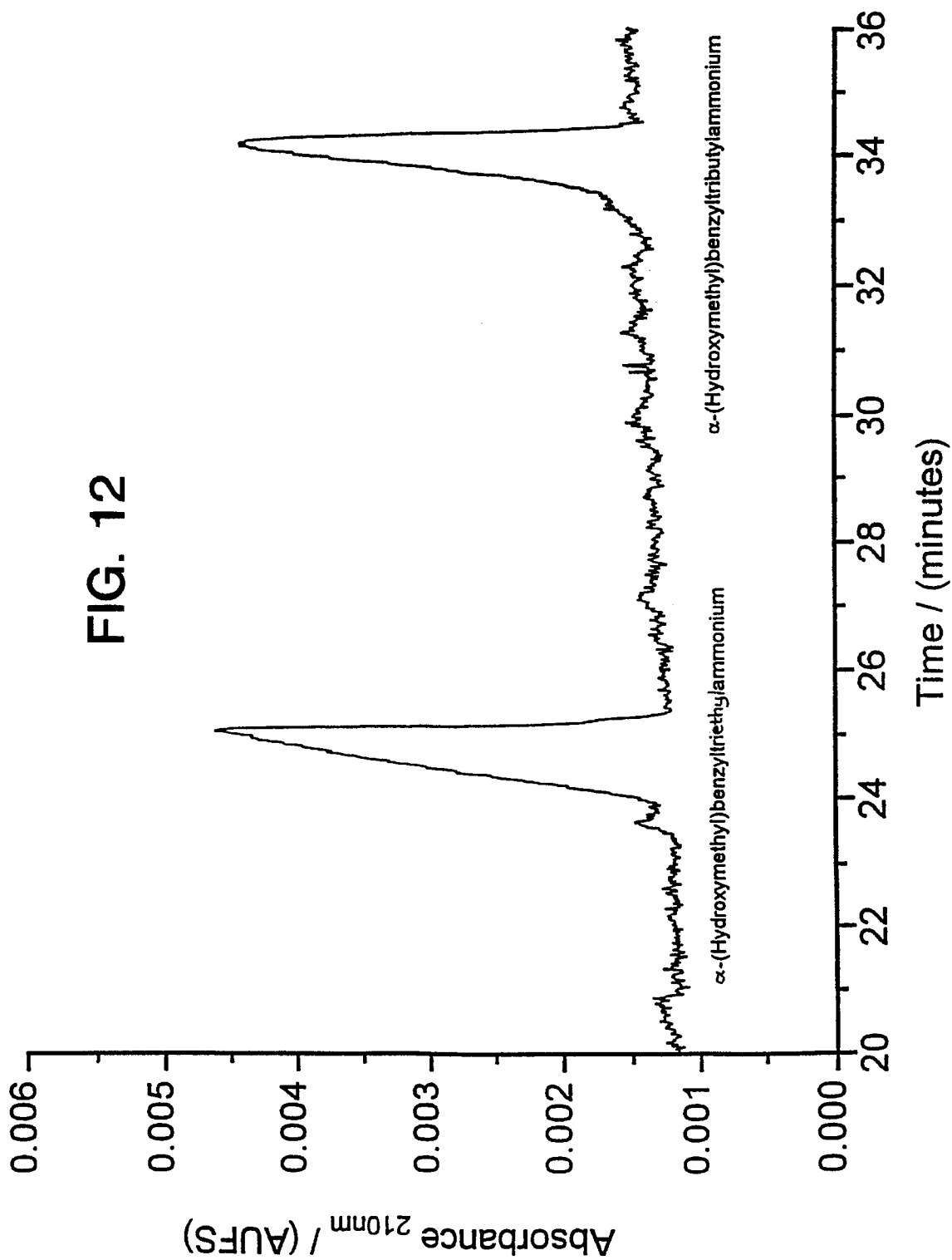
FIG. 12 depicts electrophoretic separation of the following analytes: α-(hydroxymethyl)benzyltriethylammonium ion and α-(hydroxymethyl)benzyltributylammonium ion using an electrolyte composition including about 50 mM phosphoric acid solution, the pH of which was adjusted to about 2.2 by the addition of N-methyl-N-methoxy(nonaethoxy)morpholino hydroxide.

A series of electrophoretic mobility measurements were completed using electrolyte compositions which contained 50 mM reagent grade phosphoric acid as buffer component. The pH of the successive compositions was adjusted to a pH of about 2.2 with the assayed solutions of N-alkyl-N-methoxy(oligoethoxy) morpholine hydroxides. A test mixture containing aromatic amine solutes with a broad range of mobilities was injected into each background electrolytes and the peak asymmetries of the test analytes were determined. Logarithms of peak asymmetries are shown in FIG. 9 as a function of the mobilities of the test solutes in the electrolyte composition containing N-methyl-N-methoxy-(ethoxy)morpholine ion. In FIG. 10, the logarithms of peak asymmetries are depicted as a function of the mobilities of the test solutes in the electrolyte composition containing N-methyl-N-methoxy(nonaethoxy)morpholine ion. Compounds with mobilities below about $31 \times 10^{-5}$ cm$^2$/Vs tail in the electrolyte composition containing N-methyl-N-methoxyethoxymorpholine ion. Compounds with mobilities above about $20 \times 10^{-5}$ cm$^2$/Vs front in the electrolyte composition containing N-methyl-N-methoxy(nonaethoxy)morpholine ion. The Fergusson plot of the N-alkyl-N-methoxy(oligoethoxy) morpholine ions, i.e., the effective mobilities of the N-alkyl-N-methoxy(oligoethoxy) morpholine ions as a function of the ⅔rd power of their molecular weight, shown in FIG. 11, allows an analyst to select a matching co-ion for a particular separation, without changing either the pH or the ionic strength of the background electrolyte. The electropherogram of a test analyte obtained with N-methyl-N-methoxy(nonaethoxy)morpholine cation as the mobility matching ion is shown in FIG. 12.

EXAMPLE IV

Figure 13:
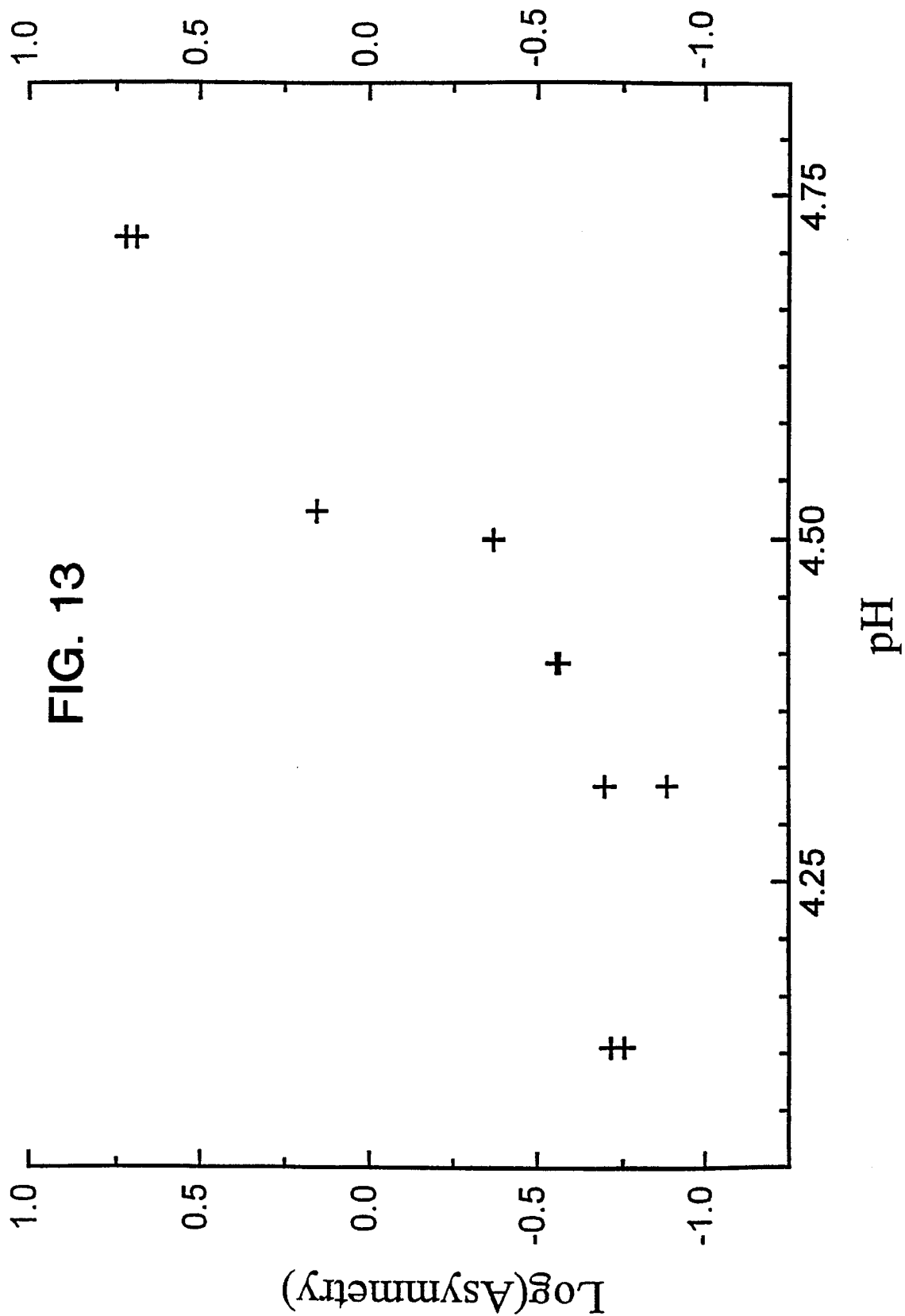
FIG. 13 depicts the logarithm of peak asymmetry as a function of the pH of the morpholinoethane sulfonic acid containing electrolyte.
Figure 14:
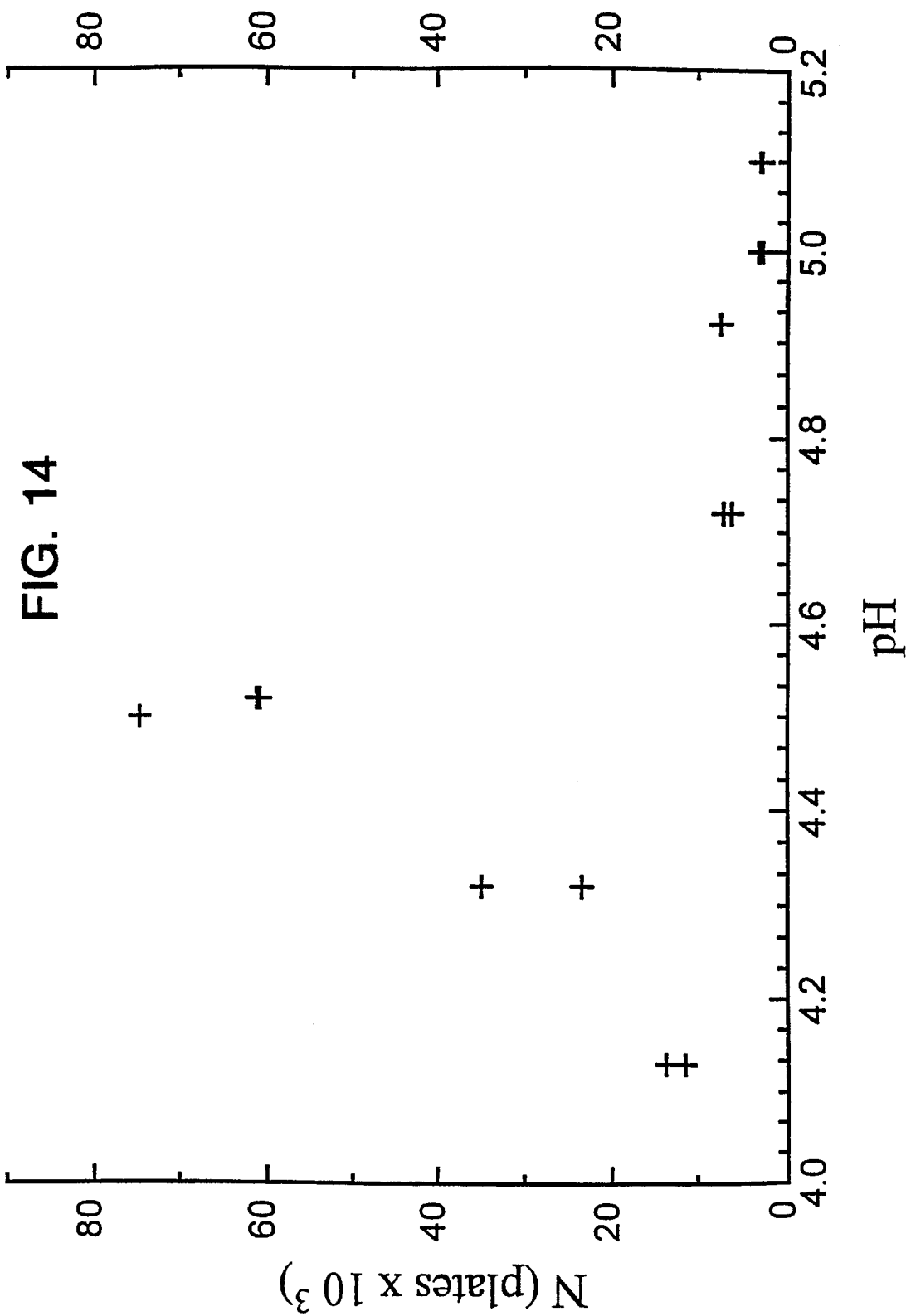
FIG. 14 depicts the separation efficiencies, expressed as plate numbers, as a function of the pH of the morpholinoethane sulfonic acid containing electrolyte composition.

A series of electrophoretic mobility measurements were completed using electrolyte compositions which contained about 200 mM reagent grade morpholinoethane sulfonic acid monohydrate, MES, as buffer component, about 0.2% 250 MHR PA hydroxyethyl cellulose, HEC manufactured by Aqualon Company, Wilmington, Del., as electroosmotic flow-controlling reagent, and about 15 mM β-cyclodextrin manufactured by American Maize Products Corporation, Hammond, Ind., as complexing agent. The pH of the electrolyte composition was adjusted with NaOH, such that the pH was greater than about 4.15 and less than about 5.5. The peak asymmetry values and the number of theoretical plates were determined for the less mobile enantiomer of the nonsteroidal antiinflammatory drug fenoprofen, which was used as test analyte. Peak asymmetry again was calculated as A=b/a, where a is the time difference between the peak front at about 10% peak height and the peak maximum, and b is the time difference between the peak tail at about 10% peak height and the peak maximum. Logarithm of peak asymmetry is depicted in FIG. 13 as a function of pH. The separation efficiencies, expressed as plate numbers, are shown in FIG. 14. Below a pH of about 4.4, the peaks of the fenoprofen enantiomers front, and the corresponding separation efficiencies are low. The peak shape improves as pH increases from about 4.45 to about 4.55, and the separation efficiencies reach as high as 75,000 plates. Above a pH of about 4.6, the peaks of the fenoprofen enantiomers tail, and the separation efficiencies decrease drastically.

EXAMPLE V

Figure 15:
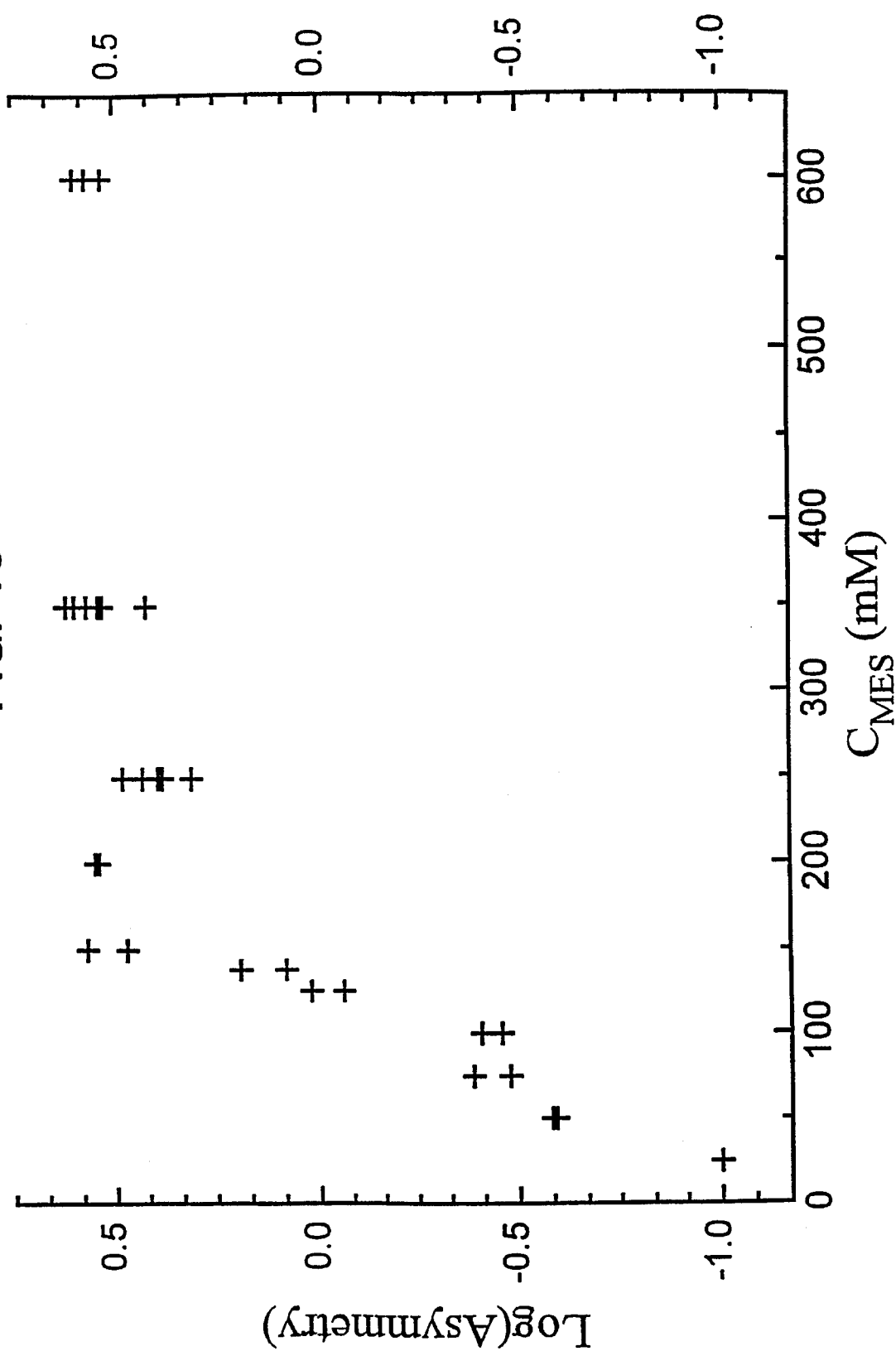
FIG. 15 depicts the logarithm of peak asymmetry as a function of the analytical concentration of morpholinoethane sulfonic acid with a pH of about 4.65 and β-cyclodextrin concentration of about 15 mM.
Figure 16:
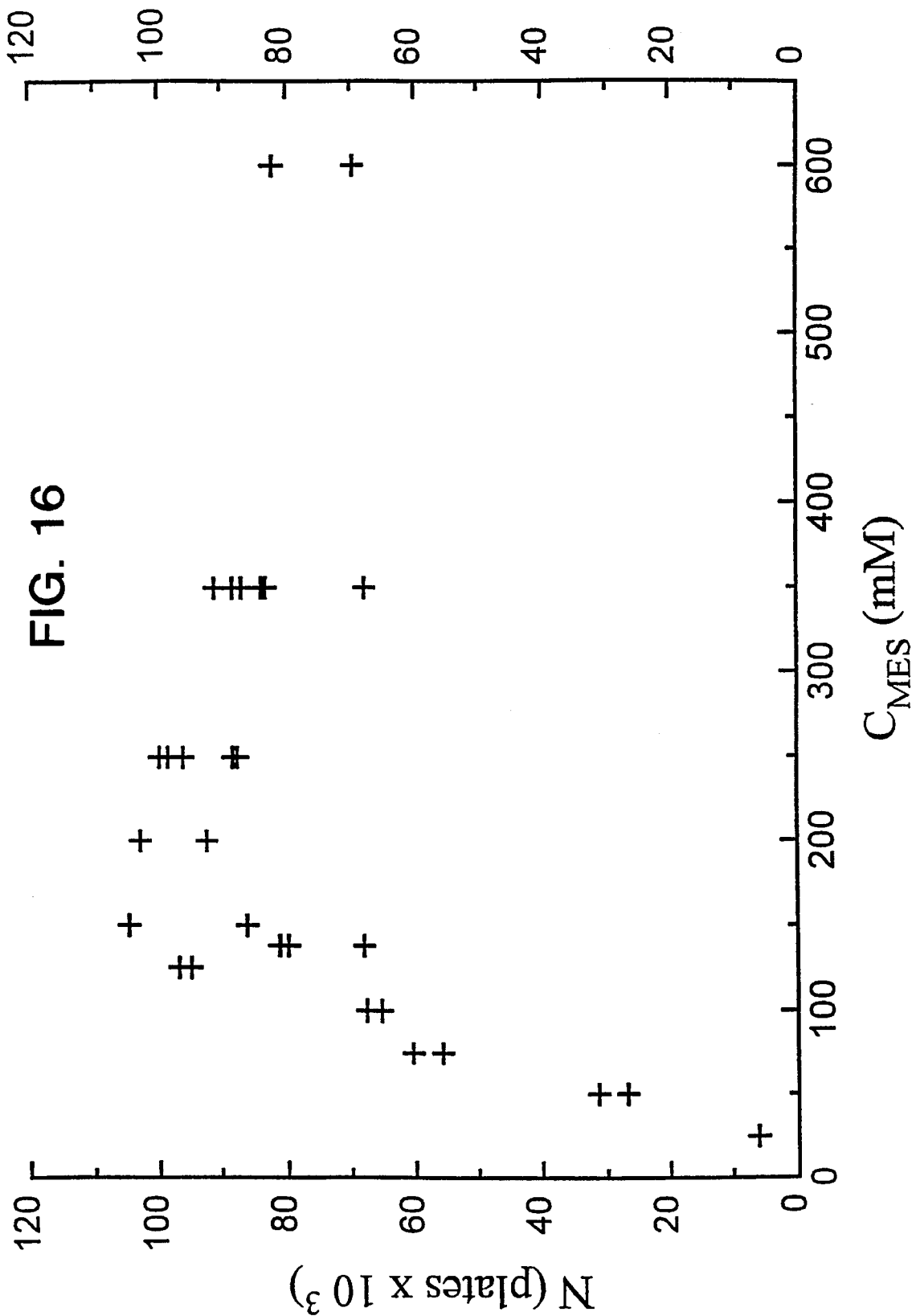
FIG. 16 depicts the separation efficiencies, expressed as plate numbers, as a function of the analytical concentration of morpholinoethane sulfonic acid with a pH of about 4.65 and β-cyclodextrin concentration of about 15 mM.

A series of capillary electrophoretic separations were completed using electrolyte compositions in which pH was maintained at about 4.65, the cyclodextrin concentration was maintained at about 15 mM, and the concentration of morpholinoethane sulfonic acid was varied in a range of about 20 to 600 mM. Peak asymmetry values and system efficiency values were determined as in Example IV for the less mobile enantiomer of fenoprofen. The logarithm of peak asymmetry is shown in FIG. 15 as a function of the analytical concentration of morpholinoethane sulfonic acid. The corresponding plate numbers are shown in FIG. 16. When the analytical concentration of morpholinoethane sulfonic acid is less than about 100 mM, the fenoprofen peaks front, and separation efficiencies are low. When the analytical concentration of morpholinoethane sulfonic acid is increased to a value in a range of about 110 to 130 mM, the peaks become symmetrical, and separation efficiencies reach as high as about 105,000 plates. When the analytical concentration of morpholinoethane sulfonic acid is increased above about 150 mM, however, the peaks begin to tail, and separation efficiency decreases again. See FIG. 16.

Figure 17:
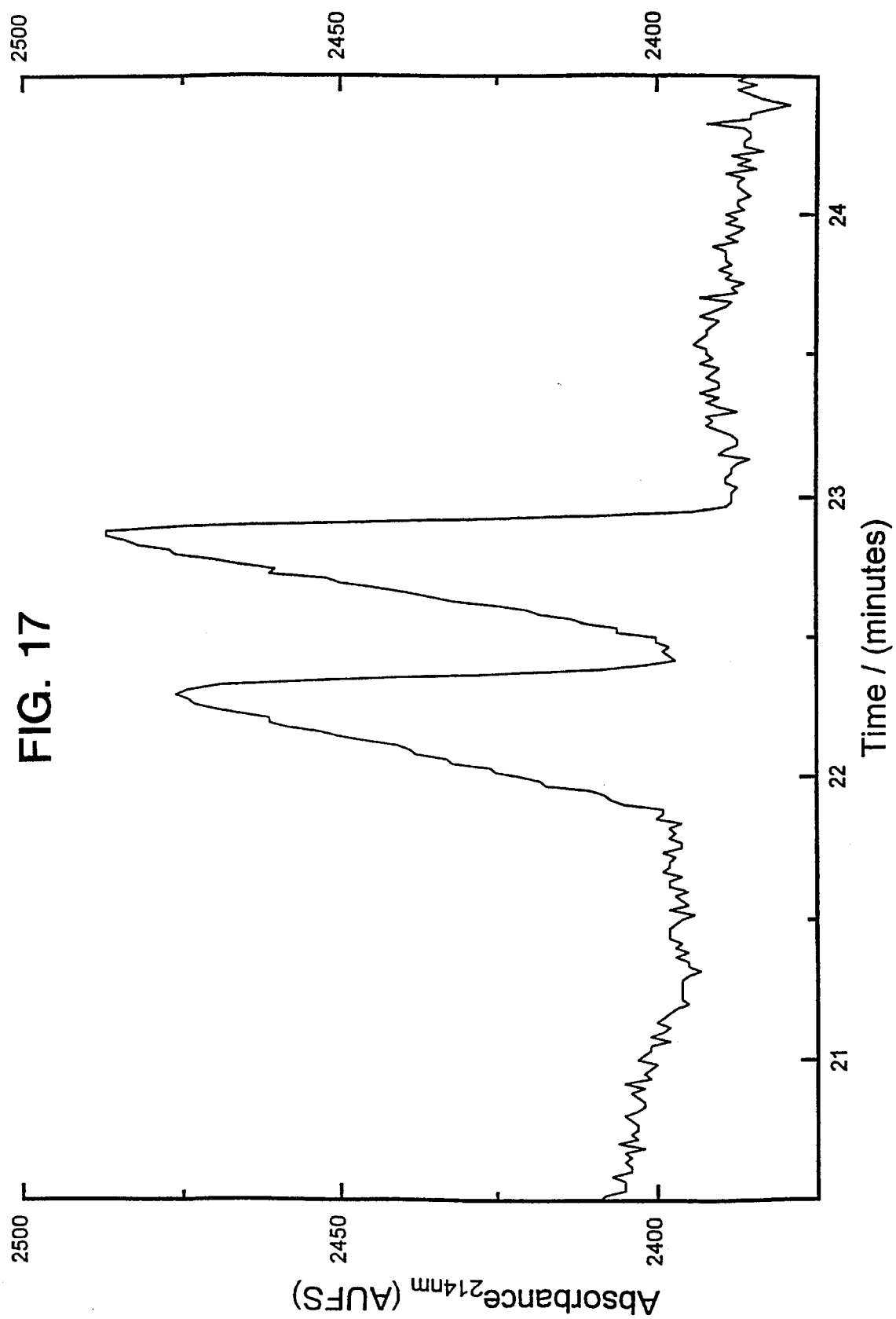
FIG. 17 depicts electrophoretic separation of the enantiomers of fenoprofen using an electrolyte composition with a pH of about 4.65 which contains about 50 mM of morpholinoethane sulfonic acid and about 15 mM of β-cyclodextrin, wherein the separation led to fronting peaks.
Figure 18:
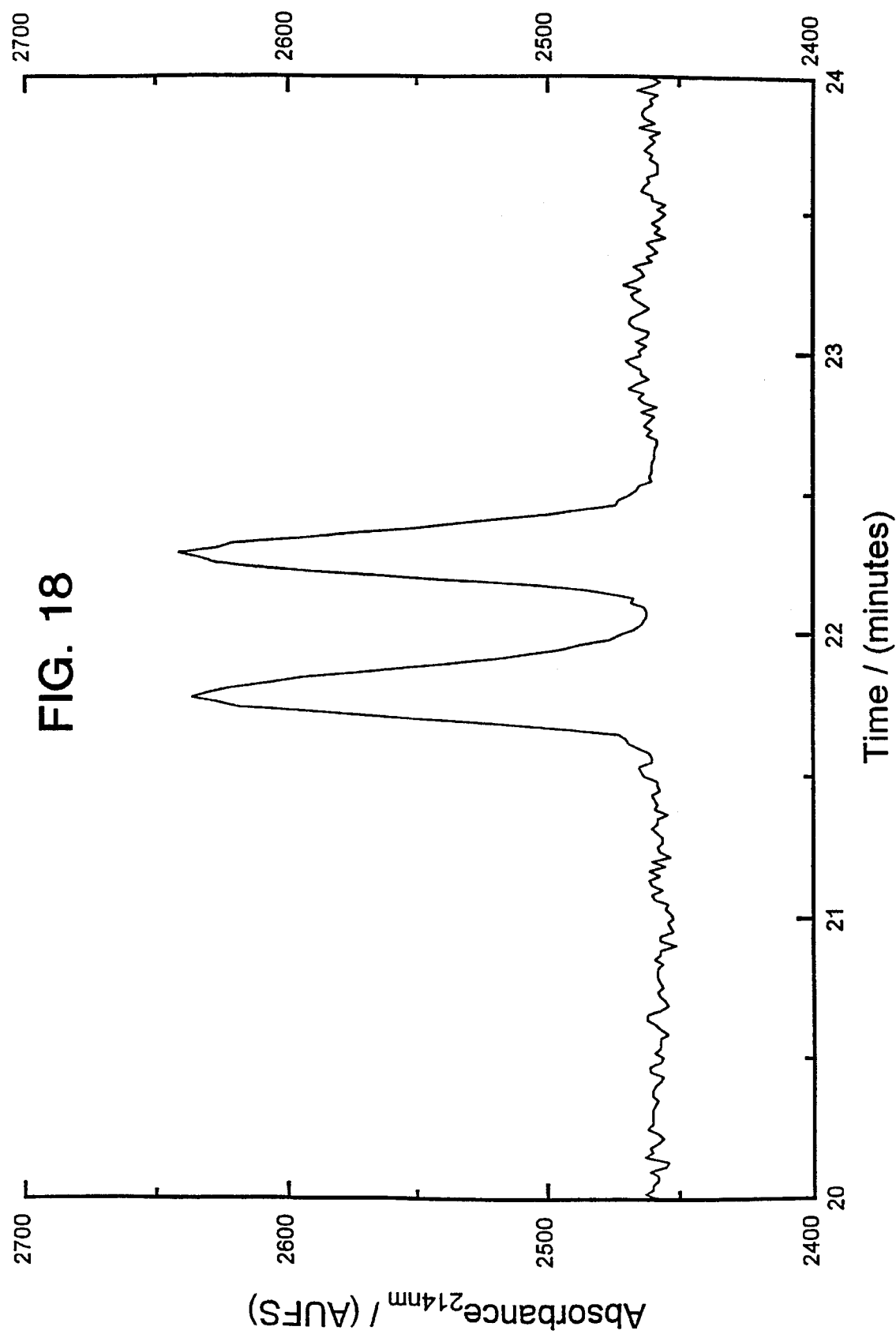
FIG. 18 depicts electrophoretic separation of the enantiomers of fenoprofen using an electrolyte composition with a pH of about 4.65, which contains about 113 mM of morpholinoethane sulfonic acid and about 15 mM of β-cyclodextrin, wherein the separation led to symmetric peaks.
Figure 19:
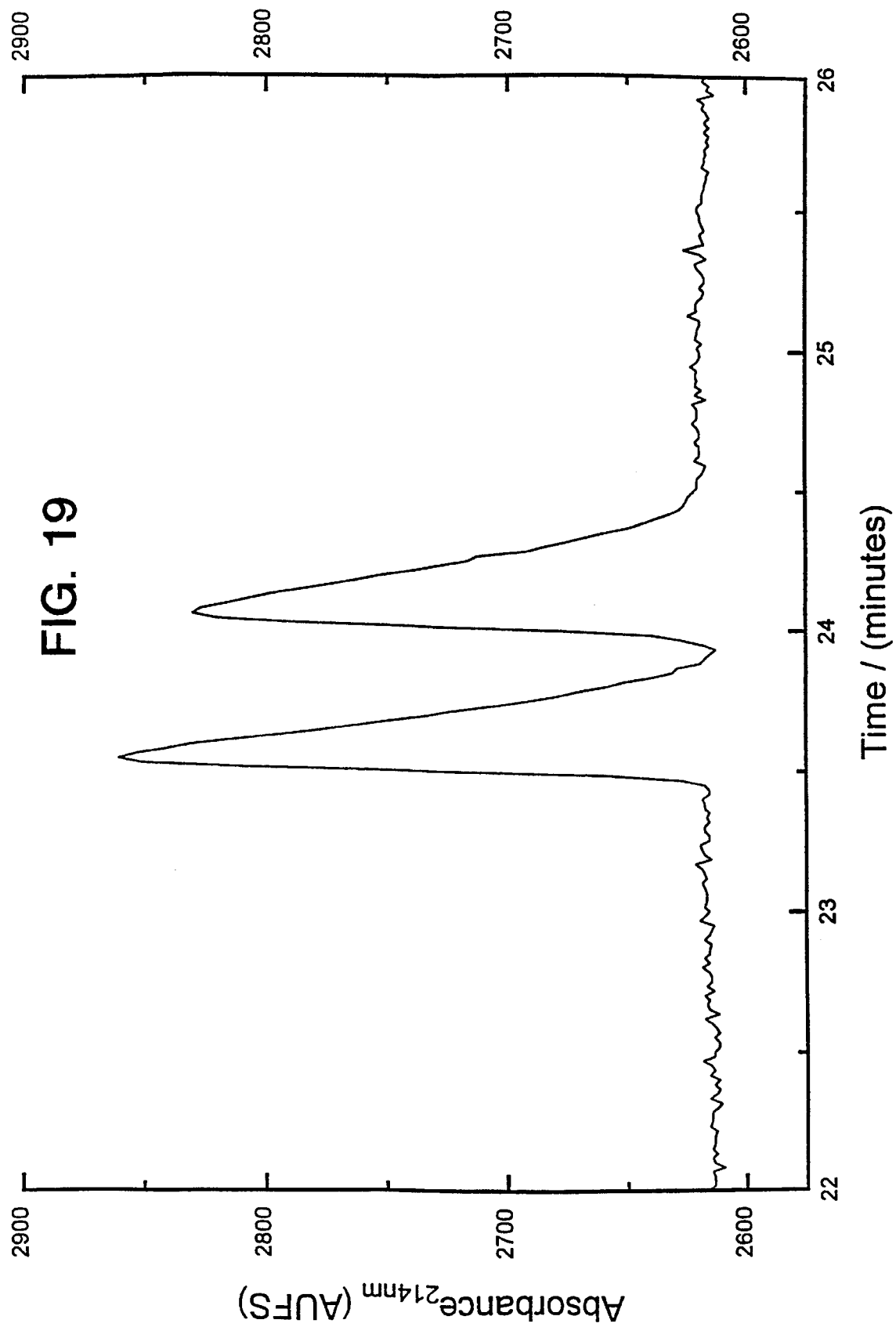
FIG. 19 depicts electrophoretic separation of the enantiomers of fenoprofen using an electrolyte composition with a pH of about 4.65 which contains about 600 mM of morpholinoethane sulfonic acid and about 15 mM of β-cyclodextrin, wherein the separation led to tailing peaks.

The electropherogram of the enantiomers of fenoprofen in an electrolyte composition with a pH of about 4.65, which contains morpholinoethane sulfonic acid at an analytical concentration of about 50 mM, is shown in FIG. 17. The electropherogram in an electrolyte composition with a pH of about 4.65 which contains morpholinoethane sulfonic acid at an analytical concentration of about 113 mM is shown in FIG. 18. Moreover, the electropherogram of the enantiomers of fenoprofen in an electrolyte composition with a pH of about 4.65 which contains morpholinoethane sulfonic acid at an analytical concentration of about 600 mM is shown in FIG. 19. While the migration times and separation selectivities change relatively little, the peak shapes go from fronting through symmetric to tailing, and separation efficiency increases to a peak and then decreases.

In another embodiment of the invention, a kit may be composed of at least one weak acid or weak base to provide the buffering function, and several strong acids or strong bases or their salts, the mobilities of which can vary in a range of about $1 \times 10^{-7}$ to $300 \times 10^{-4}$ cm$^2$/Vs, to provide the mobility matching functions. Each of these components of the kit may be included as either neat substances, e.g., powders or liquids, or solutions, and may be mixed prior to the electrophoretic separations, as outlined above in Examples I–III, to produce the desired solution pH and the symmetric analyte peak shapes. In an alternative embodiment, the kit may be composed of at least one weak acid or weak base to provide the buffering function and at least one complexing agent to vary the mobilities of the buffer system in a range of about $1 \times 10^{-7}$ to $300 \times 10^{-4}$ cm$^2$/Vs, to provide the mobility matching functions. Once again, the kit components may be included as either neat substances, e.g., powders or liquids, or solutions, and may be mixed prior to the electrophoretic separations, as outlined in Example V, to produce the desired solution pH and the symmetric analyte peak shapes.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

I claim:

1. An electrolyte composition for use in electrophoresis to separate a charged analyte having a mobility $\mu_a$ in an electric field, wherein said composition has a pH, comprising:

at least one buffer system and mobility matching ions having a mobility $\mu_2$ in said electric field, such that $\mu_a/\mu_2$ equals about one.

2. The electrolyte composition of claim 1, wherein the pH is within a pH range of about 2 to 12, and $\mu_2$ remains substantially constant over the pH range.

3. The electrolyte composition of claim 1, wherein the pH is within a pH range selected from the group consisting of about 3 to 5, about 4 to 6, about 7 to 9, and about 8 to 10, and $\mu_2$ remains substantially constant over the pH range.

4. The electrolyte composition of claim 1, wherein the pH is within a pH range selected based on said analyte to be separated, and $\mu_2$ remains substantially constant over the pH range.

5. The electrolyte composition of claim 1, wherein each of said mobilities has an absolute value less than about $300 \times 10^{-4}$ cm$^2$/Vs.

6. The electrolyte composition of claim 1, wherein said analyte is an anion, said at least one buffer system is a conjugate acid buffer system, and said matching ions have a charge of the same sign as said analyte.

7. The electrolyte composition of claim 1, wherein said analyte is a cation, said at least one buffer system is a conjugate base buffer system, and said matching ions have a charge of the same sign as said analyte.

8. The electrolyte composition of claim 1, wherein said matching ions are selected from the group consisting of quaternary ammonium moieties, sulfonate moieties, and sulfate moieties.

9. The electrolyte composition of claim 10, wherein each of said mobilities has an absolute value less than about $300 \times 10^{-4}$ cm$^2$/Vs.

10. The electrolyte composition of claim 1, wherein said matching ions are selected from the group of acids consisting of RSO$_3$H and RSO$_4$H, wherein R is a moiety selected from the group consisting of alkyls, alkylenes, substituted alkyls, aryls, substituted aryls, cycloalkyls, substituted cycloalkyls, polyoxyethylenes, polyoxyalkylenes, and polysaccharides.

11. The electrolyte composition of claim 1, wherein said matching ions are selected from the group of bases consisting (R$_1$)(R$_2$)(R$_3$)(R$_4$)NOH, (R$_1$)(R$_2$)(Cycl$_1$)NOH, and (R$_1$)(Cycl$_2$)NOH, wherein R$_1$, R$_2$, R$_3$, and R$_4$ are selected from the group of moieties consisting of alkyls, substituted alkyls, aryls, substituted aryls, cycloalkyls, substituted cycloalkyls, polyoxyethylenes, polyoxyalkylenes, and polysaccharides; Cycl$_1$ is a structure with two bonds to N; and Cycl$_2$ is a structure with three bonds to N.

12. A method of electrophoresis to separate a charged analyte having a mobility $\mu_a$ in an electric field, comprising the steps of:

providing an electrolyte composition comprised of at least one buffer system including concentrations of neutral and ionic components and mobility matching ions having a mobility $\mu_2$ in said electric field, wherein said composition has a pH;

altering the pH, such that the mobility $\mu_2$ remains substantially constant, by adjusting the concentration ratio of said neutral and ionic components of said at least one buffer system;

altering the mobility $\mu_2$, such that pH remains substantially constant and $\mu_a/\mu_2$ equals about one; and electrophoresing said analyte in said composition.

13. The method of claim 12, wherein the pH is altered to within a pH range of about 2 to 12.

14. The method of claim 12, wherein the pH is altered to within a pH range selected from the group consisting of about 3 to 5, about 4 to 6, about 7 to 9, and about 8 to 10.

15. The method of claim 12, wherein the pH is altered to within a pH range selected based on said analyte to be separated.

16. The method of claim 12, wherein each of said mobilities has an absolute value less than about $300 \times 10^{-4}$ cm$^2$/Vs.

17. The method of claim 12, wherein said matching ions have a charge of the same sign of said analyte.

18. The method of claim 12, wherein said matching ions are selected from the group consisting of quaternary ammonium moieties, sulfonate moieties, and sulfate moieties.

19. The method of claim 18, wherein each of said mobilities has an absolute value less than about $300 \times 10^{-4}$ cm$^2$/Vs.

20. An electrolyte composition having a pH, for use in electrophoresis to separate a charged analyte having a mobility $\mu_a$ in an electric field, comprising:

at least one buffer system including at least one ionic component having a mobility $\mu_2$ in said electric field, for maintaining the pH; and at least one complexing agent which complexes with said at least one buffer system to alter the mobility $\mu_2$, such that $\mu_a/\mu_2$ equals about one.

21. The electrolyte composition of claim 20, wherein the pH is within a pH range of about 2 to 12.

22. The electrolyte composition of claim 20, wherein the pH is within a pH range selected from the group consisting of about 3 to 5, about 4 to 6, about 7 to 9, and about 8 to 10.

23. The electrolyte composition of claim 20, wherein the pH is within a pH range selected based on said analyte to be separated.

24. The electrolyte composition of claim 20, wherein said at least one agent is an oligosaccharide.

25. The electrolyte composition of claim 20, wherein said at least one agent is selected frown the group consisting of underivatized, O-derivatized, and des-O-derivatized cyclomaltohexaoses, cyclomaltoheptaoses, and cyclomaltooctaoses.

26. The electrolyte composition of claim 20, wherein said at least one agent is selected from the group consisting of underivatized, O-derivatized, and des-O-derivatized maltoses with a degree of polymerization greater than three.

27. The electrolyte composition of claim 20, wherein said at least one agent is selected from the group consisting of underivatized, O-derivatized, and des-O-derivatized, linear, branched, and cyclic oligosaccharides with a degree of polymerization greater than three.

28. A method of electrophoresis to separate a charged analyte having a mobility $\mu_a$ in an electric field, comprising the steps of:

providing an electrolyte composition having a pH and including at least one buffer system with at least one ionic component having a mobility $\mu_2$ in said electric field, for maintaining the pH;

adding at least one complexing agent to said composition which complexes with said at least one buffer system to alter the mobility $\mu_2$, such that $\mu_a/\mu_2$ equals about one; and electrophoresing said analyte in said composition.

29. The method of claim 28, wherein the pH is within a pH range of about 2 to 12.

30. The method of claim 28, wherein the pH is within a pH range selected from the group consisting of about 3 to 5, about 4 to 6, about 7 to 9, and about 8 to 10.

31. The method of claim 28, wherein the pH is within a pH range selected based on said analyte to be separated.

32. The method of claim 28, wherein said at least one agent is an oligosaccharide.

33. The method of claim 28, wherein said at least one agent is selected from the group consisting of underivatized, O-derivatized, and des-O-derivatized cyclomaltohexaoses, cyclomaltoheptaoses, and cyclomaltooctaoses.

34. The method of claim 28, wherein said at least one agent is selected from the group consisting of underivatized, O-derivatized, and des-O-derivatized maltoses with a degree of polymerization greater than three.

35. The method of claim 28, wherein said at least one agent is selected from the group consisting of underivatized, O-derivatized, and des-O-derivatized, linear, branched, and cyclic oligosaccharides with a degree of polymerization greater than three.

36. An electrophoresis kit for separating a charged analyte having a mobility $\mu_a$ in an electric field comprising:

at least one buffer system component selected from the group consisting of weak acids and weak bases; and a plurality of mobility matching components selected from the group consisting of strong acids and strong bases and their salts having a mobility $\mu_2$ in said electric field, such that $\mu_a/\mu_2$ equals about one.

37. The kit of claim 36, wherein said mobility matching components have mobilities in a range of about $1\times10^{-7}$ to $300\times10^{-4}$ cm$^2$/Vs.

38. The kit of claim 36, wherein said components are solutions.

39. An electrophoresis kit for separating a charged analyte having a mobility $\mu_a$ in an electric field comprising:

at least one buffer system component selected from the group consisting of weak acids and weak bases having a mobility $\mu_2$ in said electric field; and at least one complexing agent component to vary the mobility of said buffer system component, which complexes with said at least one buffer system component to alter the mobility $\mu_2$, such that $\mu_a/\mu_2$ equals about one.

40. The kit of claim 39, wherein said mobility of said buffer system component is varied within a range of about $1\times10^{-7}$ to $300\times10^{-4}$ cm$^2$/Vs to match said analyte's mobility.

41. The kit of claim 39, wherein said components are solutions.

42. The kit of claim 39, wherein said at least one complexing agent component includes an oligosaccharide.

43. The kit of claim 39, wherein said at least one complexing agent component includes a complexing agent selected from the group consisting of underivatized, O-derivatized, and des-O-derivatized cyclomaltohexaoses, cyclomaltoheptaoses, and cyclomaltooctaoses.

44. The kit of claim 39, wherein said at least one complexing agent component includes a complexing agent selected from the group consisting of underivatized, O-derivatized, and des-O-derivatized maltoses with a degree of polymerization greater than three.

45. The kit of claim 39, wherein said at least one complexing agent component includes a complexing agent selected from the group consisting of underivatized, O-derivatized, and des-O-derivatized, linear, branched, and cyclic oligosaccharides with a degree of polymerization greater than three.

\* \* \* \* \*

UNITED STATES PATENT AND TRADEMARK OFFICE
CERTIFICATE OF CORRECTION

PATENT NO. : 5,614,072
DATED : March 25, 1997
INVENTOR(S) : Gyula VIGH, et al.

It is certified that error appears in the above-indentified patent and that said Letters Patent is hereby corrected as shown below:

Title page, item [73], after "University", insert --System--.

Signed and Sealed this

Twenty-eighth Day of October, 1997

Attest:

BRUCE LEHMAN

*Attesting Officer*     *Commissioner of Patents and Trademarks*